(12) United States Patent
Tu et al.

(10) Patent No.: US 8,575,273 B2
(45) Date of Patent: Nov. 5, 2013

(54) COUPLING AGENTS AND COMPOSITIONS PRODUCED USING THEM

(75) Inventors: Huilin Tu, Cambridge, MA (US); Agathe Robisson, Cambridge, MA (US); Julien Ramier, Cheltenham (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 549 days.

(21) Appl. No.: 12/324,104

(22) Filed: Nov. 26, 2008

(65) Prior Publication Data

US 2010/0130687 A1 May 27, 2010

(51) Int. Cl.
*C08L 27/12* (2006.01)

(52) U.S. Cl.
USPC .......................................... 525/199; 523/213

(58) Field of Classification Search
USPC .......................................... 525/199; 523/213
See application file for complete search history.

(56) References Cited

U.S. PATENT DOCUMENTS

| | | | |
|---|---|---|---|
| 4,308,372 A | 12/1981 | Smith et al. | |
| 4,660,637 A | 4/1987 | McGill et al. | |
| 4,694,045 A | 9/1987 | Moore | |
| 4,860,581 A | 8/1989 | Zimmerman et al. | |
| 4,936,139 A | 6/1990 | Zimmerman et al. | |
| 5,026,786 A | 6/1991 | Marchionni et al. | |
| 5,266,650 A | 11/1993 | Guerra et al. | |
| 5,311,952 A | 5/1994 | Eddison et al. | |
| 5,384,374 A | 1/1995 | Guerra et al. | |
| 5,617,926 A | 4/1997 | Eddison et al. | |
| 5,674,959 A | 10/1997 | Arcella et al. | |
| 5,717,036 A | 2/1998 | Saito et al. | |
| 5,727,641 A | 3/1998 | Eddison et al. | |
| 6,186,227 B1 | 2/2001 | Vaynshteyn et al. | |
| 6,419,014 B1 | 7/2002 | Meek et al. | |
| 7,289,285 B2 | 10/2007 | Barnes | |
| 7,331,581 B2 | 2/2008 | Xu et al. | |
| 7,363,970 B2 | 4/2008 | Corre et al. | |
| 7,392,851 B2 | 7/2008 | Brennan, III et al. | |
| 2007/0112149 A1 | 5/2007 | Hara et al. | |

FOREIGN PATENT DOCUMENTS

| | | | |
|---|---|---|---|
| CA | 2067891 A1 | | 11/1992 |
| EP | 310966 B1 | | 9/1988 |
| EP | 222201 B1 | | 7/1990 |
| EP | 0784064 A1 | | 7/1997 |
| JP | 3014838 | | 1/1991 |
| JP | 3163148 | | 7/1991 |
| JP | 5039294 | | 2/1993 |
| JP | 6256567 | | 9/1994 |
| JP | 11-012330 | * | 1/1999 |
| JP | 2003138127 | | 5/2003 |
| JP | 2004131543 | | 4/2004 |
| JP | 2007161999 | | 6/2007 |

OTHER PUBLICATIONS

JP 11 012330 Machine Translation (1999).*
Caporiccio et al, "A new perfluorinated grease for high-vacuum technology", Ind. Eng. Chem. Prod. Res. Dev. 1982, 21, pp. 520-522.
Mealey et al, "Past, present and future of organosilane treatments for fillers", dowcorning.com, Rubber World, pp. 32-35, Jan. 25, 2006.
Matinlinna et al, "An introduction to silanes and their clinical applications in dentistry", International Journal of Prosthodontics, vol. 17, No. 2, pp. 155-164, 2004.
Matinlinna et al, "The effect of a 3-methacryloxypropyltrimethoxysilane and vinyltriisopropoxysilane blend and tris (3-trimethoxysilylpropyl) isocyanurate on the shear bond strength of composite resin to titanium metal", Dental Materials, vol. 20, issue 9, pp. 804-813, 2004.
Matsumoto et al, "Further discussion of steric effect on the radical polymerization of triallyl isocyanurate as compared with its isomer triallyl cyanurate: polymerization and copolymerization of corresponding trimethallyl compounds", European Polymer Journal, vol. 35, issue 2, 1999, pp. 195-199.
Caporiccio, G., Corti, C., Soldini, S., and Carniselli, G., "Perfluoropolyether Fluids for Vacuum Technologies," Industrial & Engineering Chemistry Product Research and Development, Sep. 1982, vol. 21(3): pp. 515-519.

* cited by examiner

*Primary Examiner* — Kuo-Liang Peng
(74) *Attorney, Agent, or Firm* — Bridget Laffey; Rachel E. Greene; Jakub Michna

(57) ABSTRACT

Certain embodiments described herein are directed to silane coupling agents that may be used, for example, to covalently couple a polymer to a filler. In some examples, devices that include the polymer-silane coupling agent-filler compositions are also described.

5 Claims, 33 Drawing Sheets

(VII)(a)

(VII)(b)

(VII)(c)

(VII)(d)

(VII)(e)

(VII)(f)

(VII)(g)

(VII)(h)

(VII)(i)

(VII)(j)

(VII)(k)

(VII)(l)

(VII)(m)

(VII)(n)

(VII)(o)

(VII)(p)

(VIII)(a)

(VIII)(b)

(VIII)(c)

(VIII)(d)

(VIII)(i)

(VIII)(j)

(VIII)(k)

(VIII)(l)

(VIII)(m)

(VIII)(n)

(VIII)(o)

(VIII)(p)

(XI)(a)

(XI)(b)

(XI)(c)

(XI)(d)

(XI)(e)　　　　　　　　(XI)(f)

(XI)(g)　　　　　　　　(XI)(h)

(XI)(i)

(XI)(j)

(XI)(k)

(XI)(l)

(XIII)(a)

(XIII)(b)

(XIII)(c)

(XIII)(d)

(XVII)(a)

(XVII)(b)

(XVII)(c)

(XVII)(d)

(XVII)(e)

(XVII)(f)

(XVII)(g)

(XVII)(h)

(XVII)(i)

(XVII)(j)

(XVII)(k)

(XVII)(l)

(XVIII)(e)

(XVIII)(f)

(XVIII)(g)

(XVIII)(h)

(XVIII)(i)

(XVIII)(j)

(XVIII)(k)

(XVIII)(l)

(XVIII)(m)

(XVIII)(n)

(XVIII)(o)

(XVIII)(p)

(XIX)(a)

(XIX)(b)

(XIX)(c)

(XIX)(d)

(XIX)(e)

(XIX)(f)

(XIX)(g)

(XIX)(h)

(XIX)(i)

(XIX)(j)

(XIX)(k)

(XIX)(l)

(XIX)(m)

(XIX)(n)

(XIX)(o)

(XIX)(p)

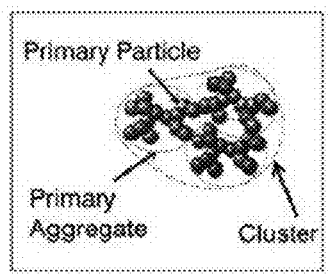
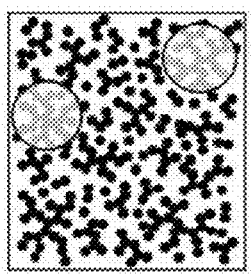
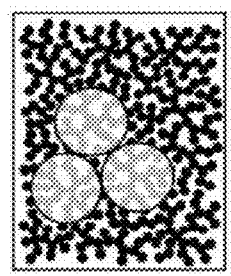
FIG. 14A     FIG. 14B     FIG. 14C
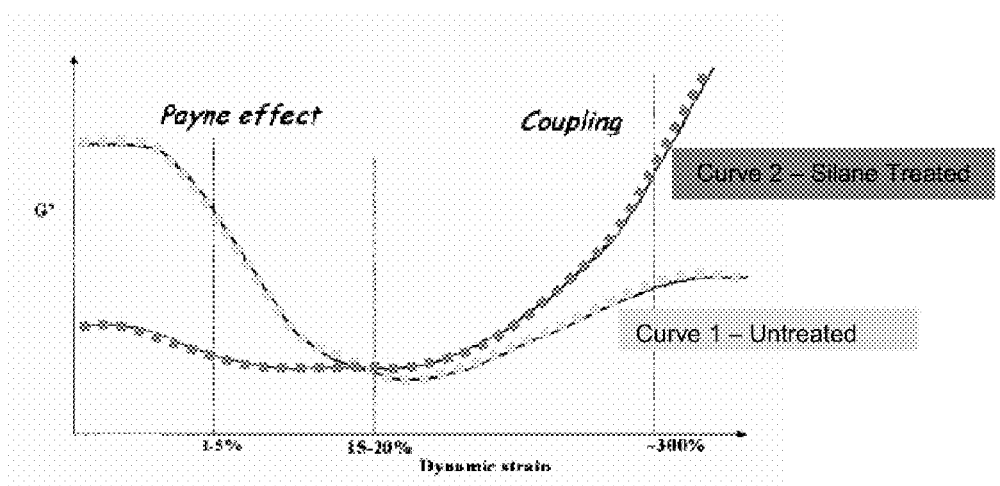
FIG. 15

(1) Initiation

COUPLING AGENTS AND COMPOSITIONS PRODUCED USING THEM

TECHNOLOGICAL FIELD

Examples disclosed herein relate generally to coupling agents and compositions produced using them. More particularly, certain embodiments disclosed herein are directed to silane coupling agents effective to covalently couple a filler to a polymer such as, for example, a fluoropolymer.

BACKGROUND

Fillers can be used with elastomer compounds and other polymers. However, very limited reinforcement effect of fillers is achieved due to the weak interactions between the fillers and the polymer.

SUMMARY

In one aspect, a composition comprising a polymer covalently coupled to a filler through a silane coupling agent, the silane coupling agent selected from the group consisting of TAIC-silane, TMAC-silane, TAC-silane and combinations thereof is provided. Illustrative polymers are described further below and include, but are not limited to a high density polyethylene, a nylon, a polycarbonate, a polyether sulfone, a polyphenylene oxide, a polyphenylene sulfide, a polypropylene, a polystyrene, a polyurethane, a polysulfone, a polyvinylchloride, a polyamide, a polyimide, a polyamide-imide, a polybutylene, a polybutylene terphthalate, a polyepoxide and other polymers. In some examples, the coupling agent may be particularly suited for use with polymers in high temperature applications such as, for example, those greater than or equal to about 150° C.

In another aspect, a composition comprising a fluoropolymer covalently coupled to a filler through a silane coupling agent, the silane coupling agent selected from the group consisting of TAIC-silane, TMAC-silane, TAC-silane and combinations thereof is provided.

In certain embodiments, the fluoropolymer can be selected from the group consisting of vinylidene fluoride (VDF), tetrafluoroethylene (TFE), hexafluoropropylene (HFP), chlorotrifluoroethylene (CTFE), perfluoro(alkylvinyl ether) (PAVE) including perfluoro(methylvinyl ether) (PMVE), vinyl fluoride (VF), ethylene (E), propylene (P) and etc. Typical fluoropolymers and perfluoropolymers (thermoplastics and elastomers) are copolymers comprising two or more above monomers. In some examples, the filler can be selected from the group consisting of precipitated silica, amorphous silica, vitreous silica, fumed silica, fused silica, quartz, glass, aluminum, aluminum-silicate (e.g., clays), copper, tin, talc, inorganic oxides (e.g. $Al_2O_3$, $Fe_2O_3$, $TiO_2$, $Cr_2O_3$), steel, iron, asbestos, nickel, zinc, silver, lead, marble, chalk, gypsum, barites, graphite, carbon black, treated carbon black. In some examples, the composition may further comprise at least one silane coupling agent having a formula as shown in formulae (XVII)(a)-(XIX)(p). In other examples, the composition may further comprise at least one of an additive, a viscosity modifier or a processing aid. In certain embodiments, substantially all of the reactive sites of the filler can be covalently coupled to the silane coupling agent.

In another aspect, a method comprising reacting a filler with at least one silane coupling agent selected from the group consisting of TAIC-silane, TMAC-silane, TAC-silane and combinations thereof to covalently couple the silane to the filler is disclosed. In certain examples, the method may further comprise reacting the covalently coupled silane-filler with a polymer to covalently couple the polymer to the covalently coupled silane-filler.

In certain embodiments, the method may comprise forming free radicals of the polymer during the reacting the covalently coupled silane-filler with a polymer step to couple the polymer at unsaturated sites of the silane of the covalently coupled silane-filler. In other examples, the method may comprise reacting the filler with the at least one silane until substantially all surface sites of the filler comprise the silane coupling agent. In additional examples, the method may comprise reacting the filler with the at least one silane coupling agent in the presence of an initiator. In some examples, the method may comprise reacting the at least one silane coupling agent with the filler in the presence of a siloxane to block functional groups on the surface of the filler to prevent reaction with the at least one silane coupling agent. In other examples, the method may comprise processing the covalently coupled polymer-silane-filler using one or more of a mixer, a mill, a mold, a calendering device and an extruder.

In an additional aspect, a compound having a formula of

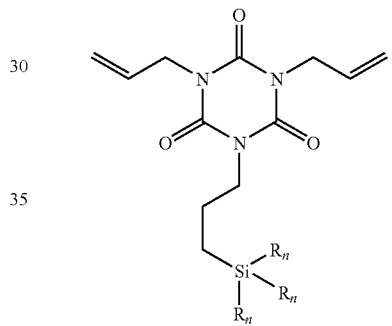

in which each $R_n$ is independently selected from the group consisting of hydroxy, methoxy, ethoxy, propoxy, chloride, bromide, dimethylamino, diethylamino and etc is provided. The compound may be used with a polymer and a filler such as, for example, those described herein.

In another aspect, a compound having a formula of

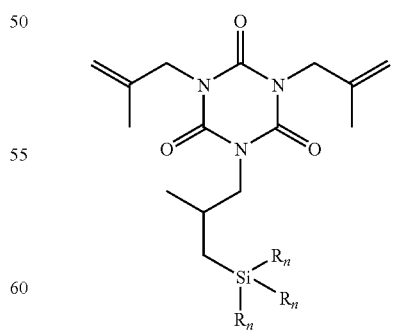

in which each $R_n$ is independently selected from the group consisting of hydroxy, methoxy, ethoxy and propoxy is disclosed. The compound may be used with a polymer and a filler such as, for example, those described herein.

In an additional aspect, a compound having a formula of

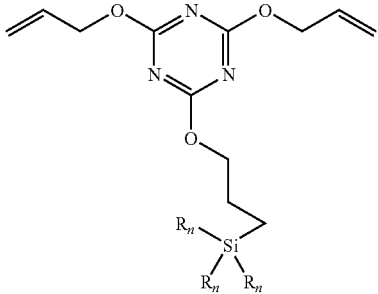

in which each $R_n$ is independently selected from the group consisting of hydroxy, methoxy, ethoxy, propoxy, chloride, bromide, dimethylamino, diethylamino and etc. is described. The compound may be used with a polymer and a filler such as, for example, those described herein.

In another aspect, a silane coupling agent having a formula as shown in formulae (XVII)(a)-(XIX)(p) is disclosed.

In an additional aspect, a silane coupling agent having a formula of $$Q_m\text{-Si}—Z_n \quad (I)$$

in which Q comprises one or more groups that provide covalent attachment to a polymer and Z comprises one or more groups that provide covalent attachment to a filler and the sum of m and n is four is disclosed.

In certain embodiments, Z is selected from a hydroxy, an alkoxy, an acyl-oxyl, a halogen, and an amine. In other embodiments, Q is a compound having a formula of

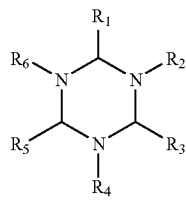

in which either $R_1$ or $R_4$ comprises a group that attaches to the Si moiety of formula (I), and in which $R_1$ and R4 are independently selected from the group consisting of C1-C6 straight chain or branched alkyl, C1-C6 straight chain or branched heteroalkyl, C1-C6 straight chain or branched alkenyl, an ester group, a keto group, an ether group, phenyl, hydrogen and oxygen, and in which each of $R_2$, $R_3$, $R_5$ and $R_6$ is independently selected from the group consisting of an alkyl group comprising two to six carbon atoms and having at least one unsaturated site and optionally containing a heteroatom. The compound may be used with a polymer and a filler such as, for example, those described herein.

In other embodiments, Q and Z are each selected to provide a compound having a formula of

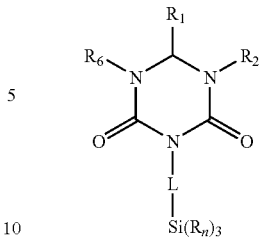

in which L is a linking group comprising one to six carbon atoms optionally including a heteroatom, in which $R_n$ is a hydrolyzable group, in which $R_1$ is selected from the group consisting of hydrogen, oxygen, methoxy, ethoxy, propoxy, an ether group, and in which each of $R_2$ and $R_6$ is independently selected from the group consisting of an alkyl group comprising two to six carbon atoms and having at least one unsaturated site and optionally containing a heteroatom. In certain embodiments, each of $R_2$ and $R_6$ is independently selected from the group consisting of propene and isopropene and L is propyl or isopropyl.

In another embodiment, Q and Z are each selected to provide a compound having a formula of

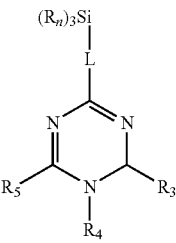

in which L is a linking group comprising one to six carbon atoms optionally including a heteroatom, in which $R_n$ is a hydrolyzable group, in which $R_4$ is selected from the group consisting of hydrogen, oxygen, methoxy, ethoxy, propoxy, an ether group or is absent, and in which each of $R_3$ and $R_5$ is independently selected from the group consisting of an alkyl group comprising two to six carbon atoms and having at least one unsaturated site and optionally containing a heteroatom. In some examples, each of $R_3$ and $R_5$ is independently selected from the group consisting of oxypropene and oxyisopropene and L is propyl or isopropyl.

In another aspect, a method of facilitating covalent coupling of a polymer to a filler, the method comprising providing a silane coupling agent having a formula as shown in formulae (I)-(XIX)(p) is provided. In certain examples, the method may also comprise providing one or more polymers and/or one or more fillers such as, for example, the illustrative polymers and fillers described herein.

Additional aspects, examples, features and embodiments of the technology will be apparent to the person of ordinary skill in the art, given the benefit of the instant specification.

BRIEF DESCRIPTION OF THE FIGURES

Certain features, aspect and examples are described in more detail below with reference to the accompanying figures in which:

FIGS. 14A-14C are illustrations showing particle dispersions and phases, in accordance with certain examples;

FIG. 15 is a graph showing the Payne effect for unmodified and silane modified fillers, in accordance with certain examples;

Figure 1A:
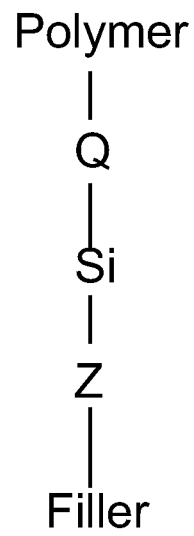
FIGS. 1A-1D are schematics of a polymer covalently coupled to a filler through a silane coupling agent, in accordance with certain examples.

It will be recognized by the person of ordinary skill in the art, given the benefit of this disclosure, that the compounds shown in the figures and used throughout the text may be shown with disproportionate bond lengths, bond angles and the like to facilitate a better understanding of the technology described herein. Unless otherwise specified, no particular stereochemistry is implied in the illustrative chemical compounds drawn and described herein.

DETAILED DESCRIPTION

Certain examples described herein provide significant advantages over existing coupling agents and materials produced using existing coupling agents including, but not limited to, reduction of the Payne effect in fillers modified with the silane coupling agents, and increased use life of parts or components produced using the materials disclosed herein. These and other advantages will be recognized by the person of ordinary skill in the art, given the benefit of this disclosure.

Certain embodiments of the polymers produced using the coupling agents disclosed herein may be used in numerous industrial, medical and mechanical applications, and are particularly suited for environments where high temperature, high pressure, aggressive chemicals and mechanical loads may be required or encountered. For example, certain embodiments of the cross-linked polymers may be particularly suited for use in oil field service (OFS) industry such as, for example, the heavy oil market in: (1) structural component and insulation applications such as electrical pads and cables, feed-through, housing and packaging material of electrical and chemical devices, valves, pumps, and etc.; (2) elastomeric applications: general-purpose seals including o-rings and gaskets, packers for exploration and production tools including inflatable packers and swellable packers, mud motor, actuators, cables and etc. Certain examples of polymers produced using the coupling agents and other materials disclosed herein may also be used in down-hole applications such as chemical, wear, and heat resistant piping, sleeves, wire and cable jacketing, coatings, connectors, liners, tubes and similar devices. In addition, the polymers disclosed herein have additional uses such as, for example, in snap fit parts, parts used in load bearing applications, heat shrinkable molded parts, and other parts used in the electrical, automotive, aerospace, medical industries and oil field service industries.

In certain embodiments, the polymers produced using the coupling agents disclosed herein may be used by themselves or in combination with one or more other polymers, metals or non-metals, or structural components to provide an assembly configured for a desired use. These and other applications and uses of the materials described herein will be readily selected by the person of ordinary skill in the art, given the benefit of this disclosure.

The compositions produced using the silane coupling agents described herein provide for covalent coupling of the polymer to the filler through the silane coupling agent. The term covalent coupling refers to attachment through one or more covalent bonds but not necessarily direct attachment to a particular species without any intervening atoms.

Fillers used in fluoroelastomer compounds are very different from those in conventional elastomers. Very limited reinforcement effects of active fillers are observed due to the very weak interactions at the interface of active fillers and fluoroelastomers. Non-active or low active carbon black or mineral fillers in loadings up to 50 phr are usually used. MT-black N990 is usually the preferred filler because of its large particle size and low structure. Other fillers including various grades of other carbon blacks, fibrous calcium silicate, barium sulfate, titanium oxide, iron oxide, silica, poly(tetrafluoroethylene) (PTFE) powders, etc. may also be used.

Strong interactions can be achieved at the filler-fluoropolymer interface if the fillers are covalently bound to the polymers. Silane coupling agents, which are capable of forming covalent bonds directly to the polymer, can be used to enhance the adhesion between the polymer and the silicate fillers. Common silane coupling agents include, but are not limited to, aminopropyltrialkoxysilane, glycidoxypropyltrialkoxysilane, mercaptopropyltrialkoxysilane and their dialkoxy-, monoalkoxy-, trichloro-, dichloro-, and monochloro-derivatives. Among them, vinyltrialkoxysilane, allyltrialkoxysilane, styrylethyltrialkoxysilane and acryloxyopropyltrialkoxysilane all have vinyl groups and may be capable of forming covalent bonds with fluoroelastomers by radical-initiated addition reactions between these vinyl groups and the vinyl groups in the curing co-agents. Some co-agents for peroxide curing of fluoroelastomers include, but are not limited to, triallylisocyanurate (TAIC), trimethallylisocyanurate (TMAIC) and triallylcyanurate (TAC).

Certain embodiments described herein are directed to thermally stable silane coupling agents which are effective to provide covalent bonding between silica fillers and fluoroelastomers, perfluoroelastomers, fluoroplastics and other polymers. The advantages provided in at least certain embodiments include, but are not limited to: (1) the reactivity of the vinyl groups in these silane coupling agents should be substantially the same as curing co-agents such as, for example, TAIC, TMAIC and TAC so that they can react very well with the polymer matrix to form cross-links providing a reinforcing effect, instead of self-polymerizing which will not help in reinforcing; (2) the thermal stability of these silanes and the produced cross-links are excellent so that reinforcing effect will be present even at high temperatures; and/or (3) similar to conventional coupling agents, these functional silanes can also improve the dispersion of silica fillers by changing their surface polarity.

Figure 1B:
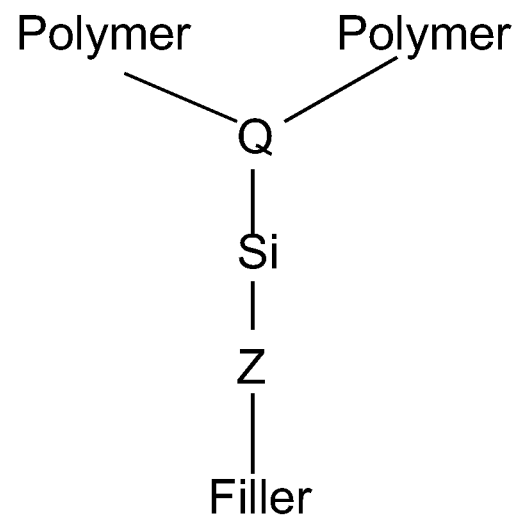
Figure 1C:
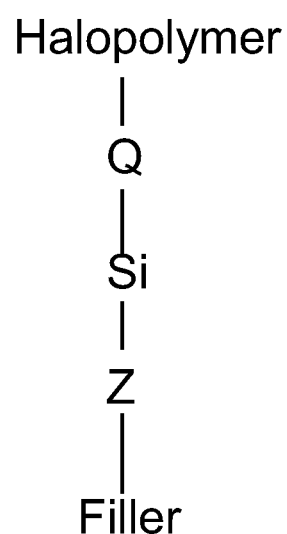
Figure 1D:
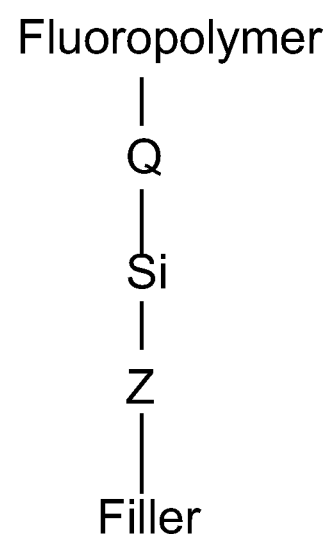
Figure 2A:
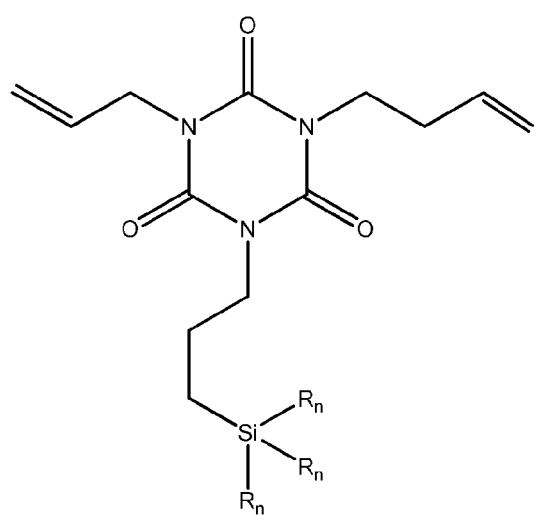
FIGS. 2A-2D show examples of formulae VII(a)-VII(p), in accordance with certain examples.
Figure 2A:
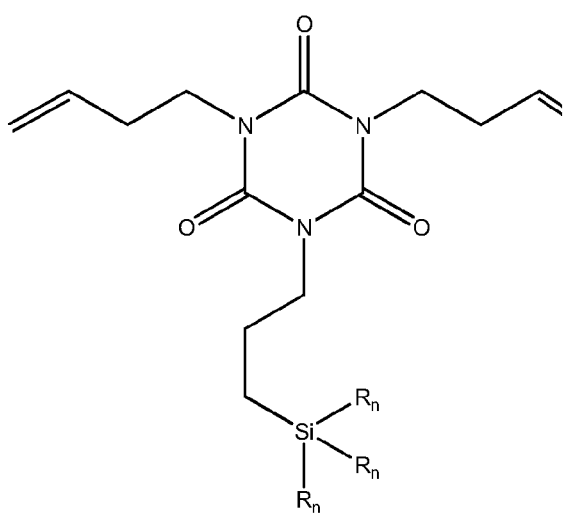
Figure 2A:
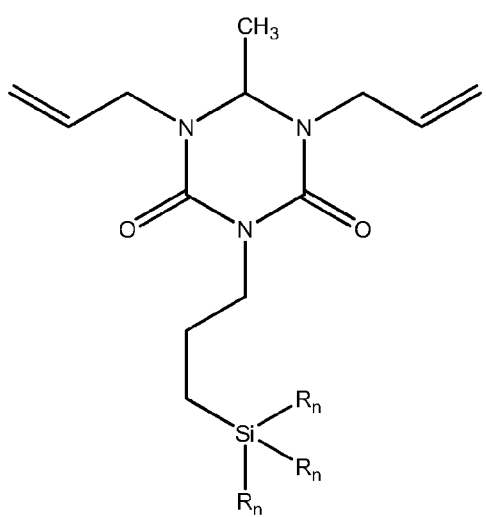
Figure 2A:
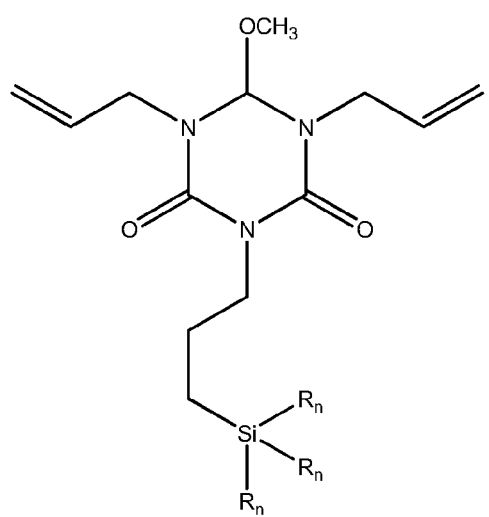
Figure 2B:
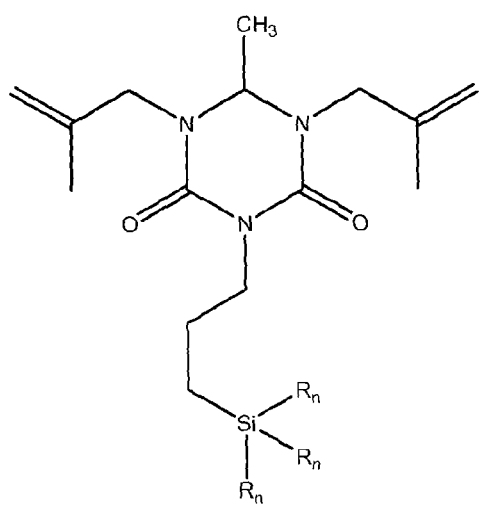
Figure 2B:
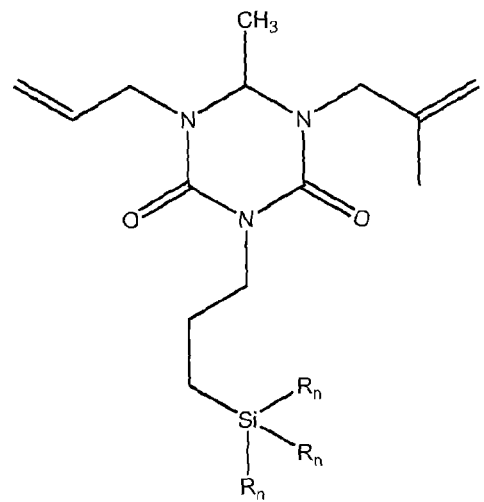
Figure 2B:
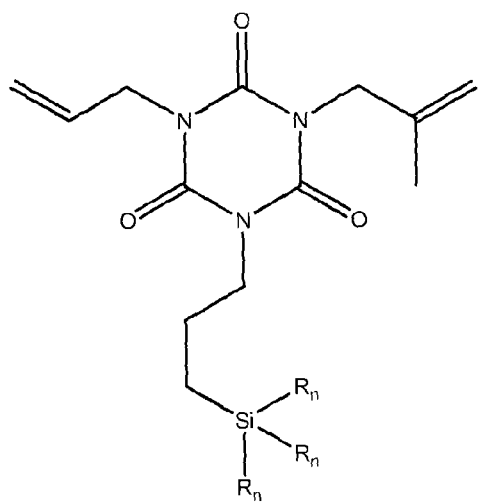
Figure 2B:
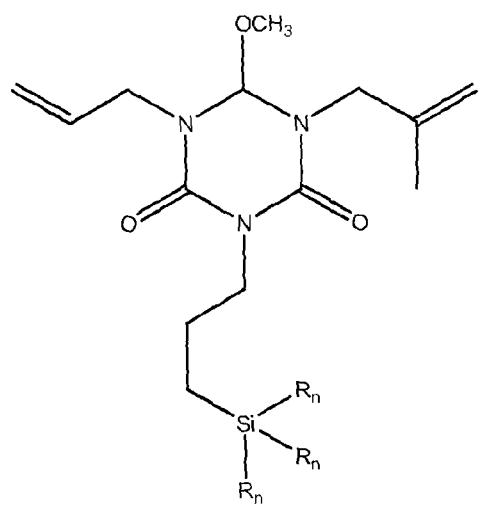
Figure 2C:
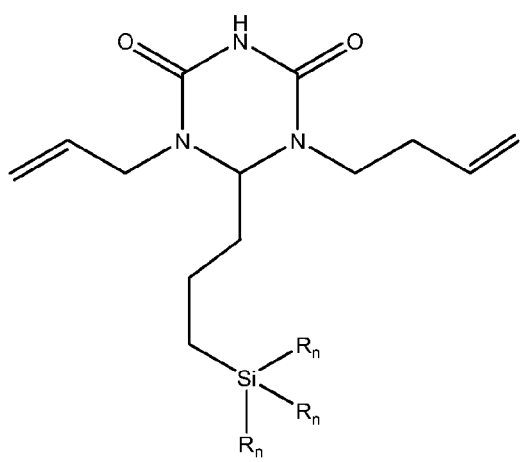
Figure 2C:
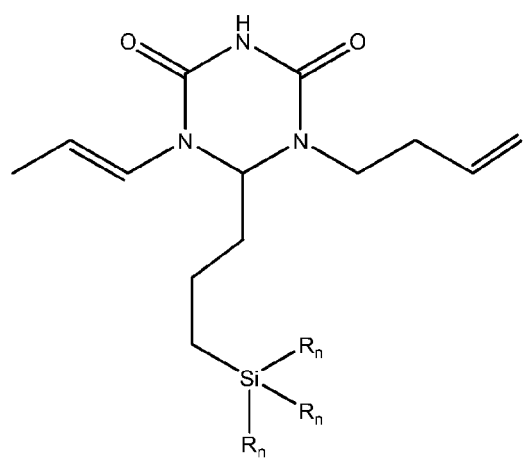
Figure 2C:
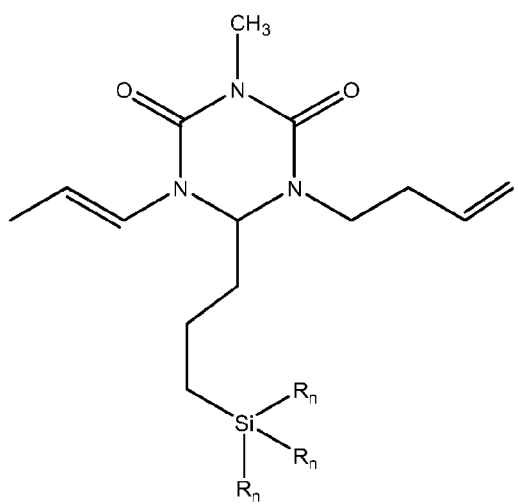
Figure 2C:
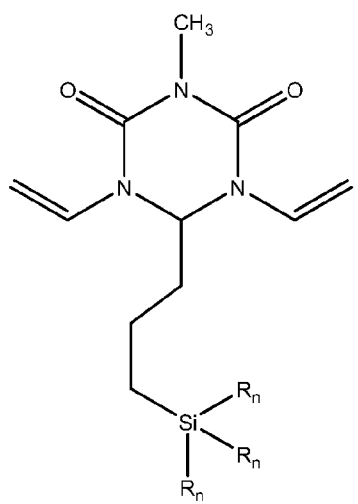
Figure 2D:
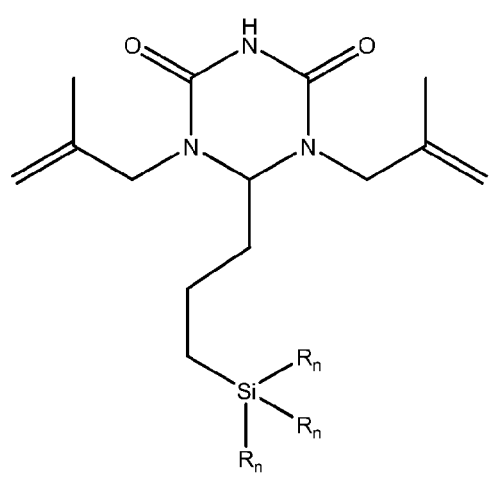
Figure 2D:
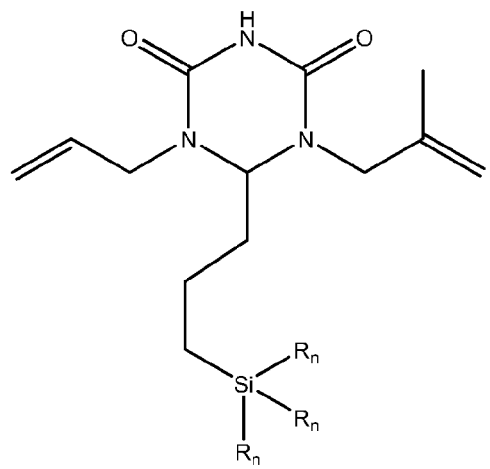
Figure 2D:
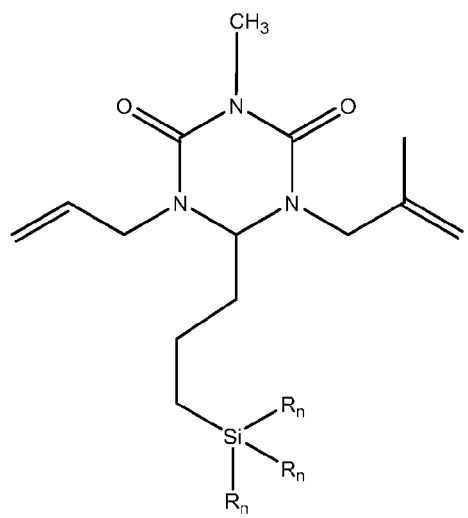
Figure 2D:
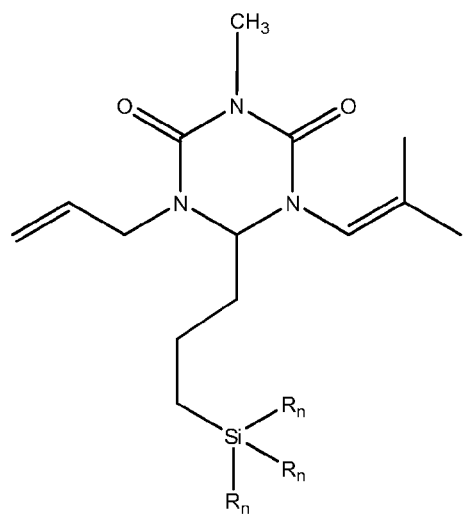
Figure 3A:
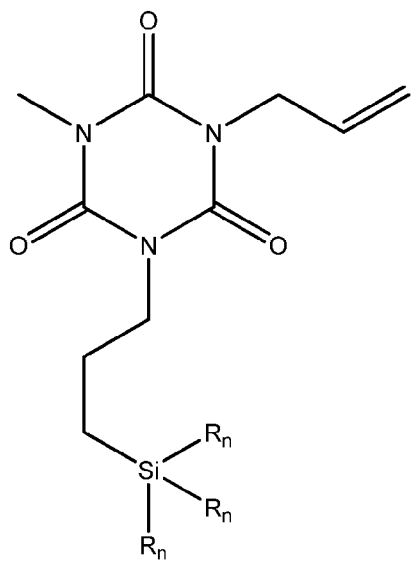
FIGS. 3A-3D show examples of formulae VIII(A)-VIII(p), in accordance with certain examples.
Figure 3A:
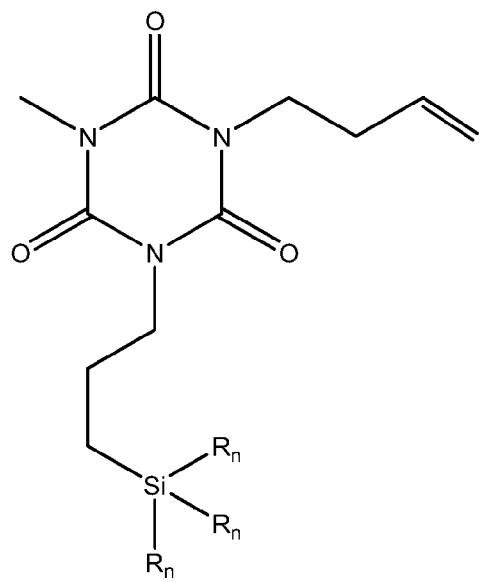
Figure 3A:
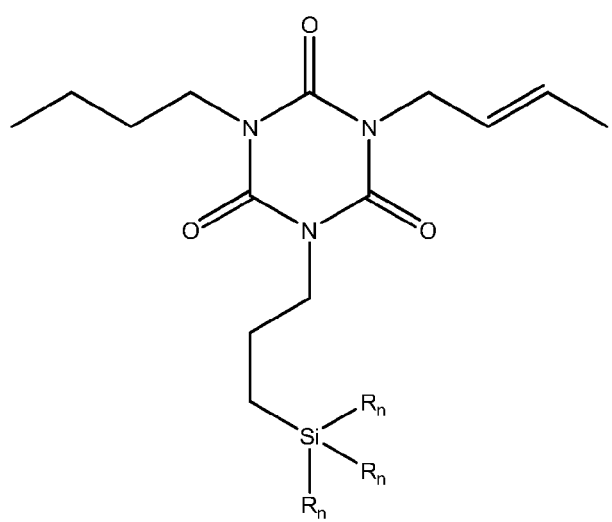
Figure 3A:
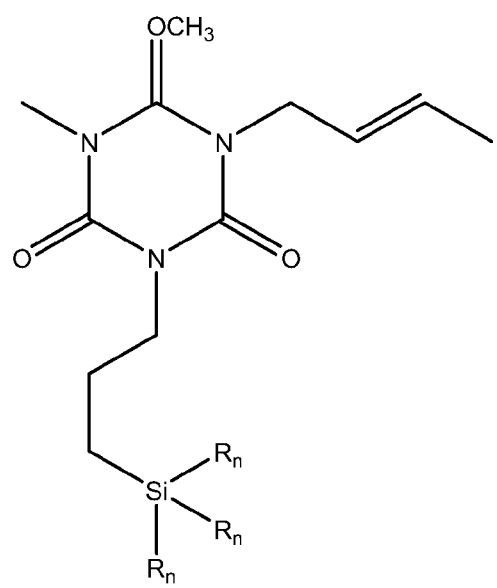
Figure 3B:
Figure 3B:
Figure 3B:
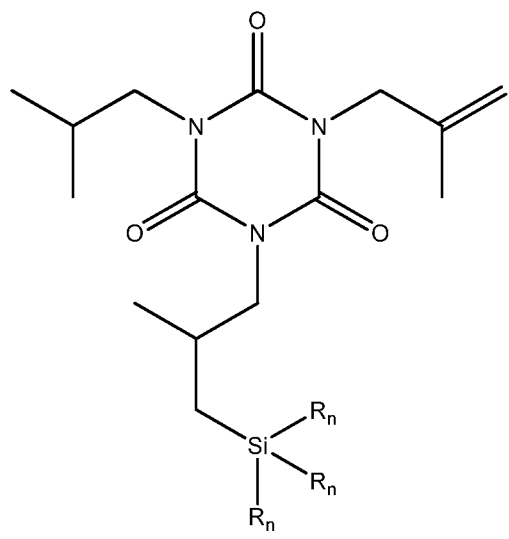
Figure 3B:
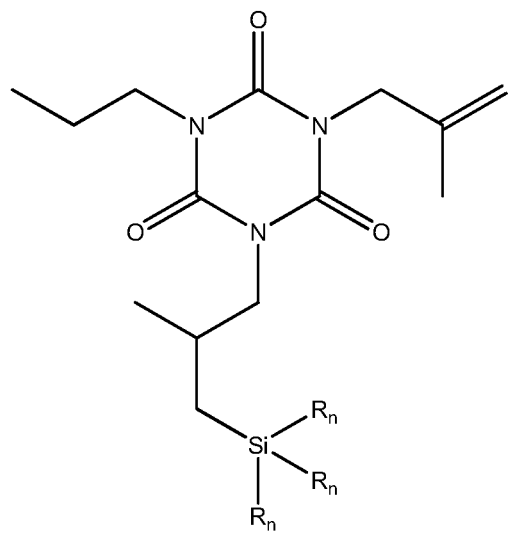
Figure 3B:
Figure 3B:
Figure 3B:
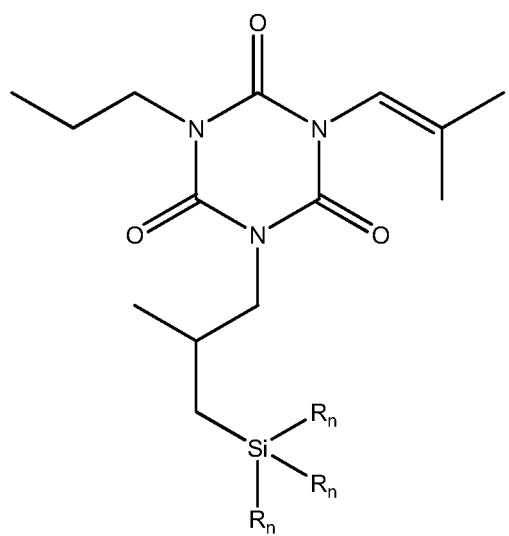
Figure 3B:
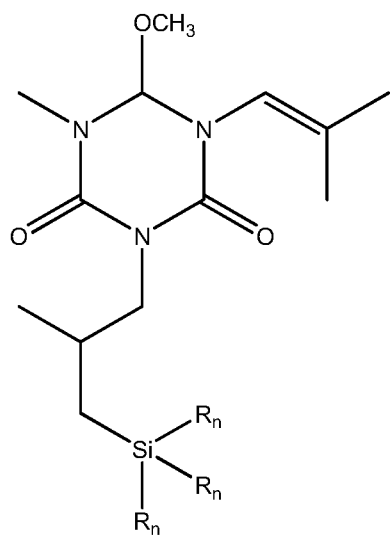
Figure 3C:
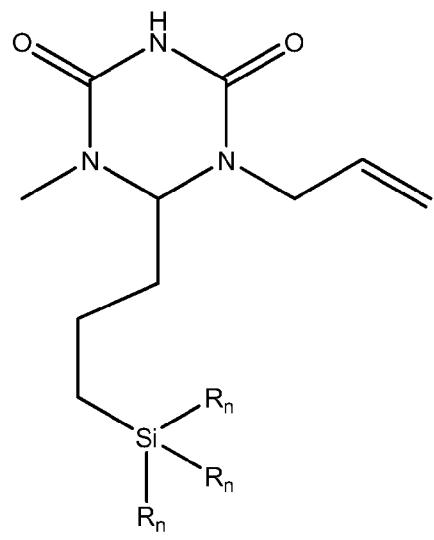
Figure 3C:
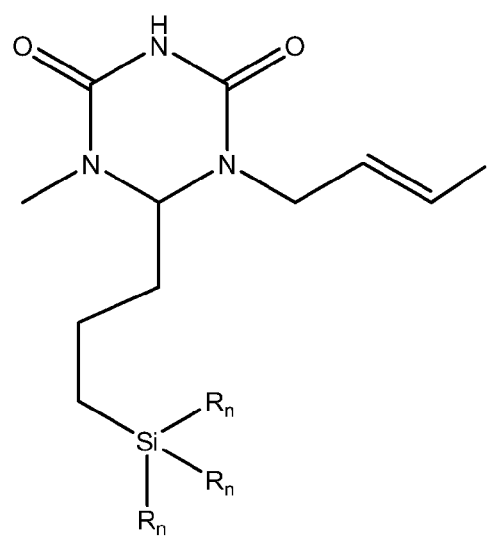
Figure 3C:
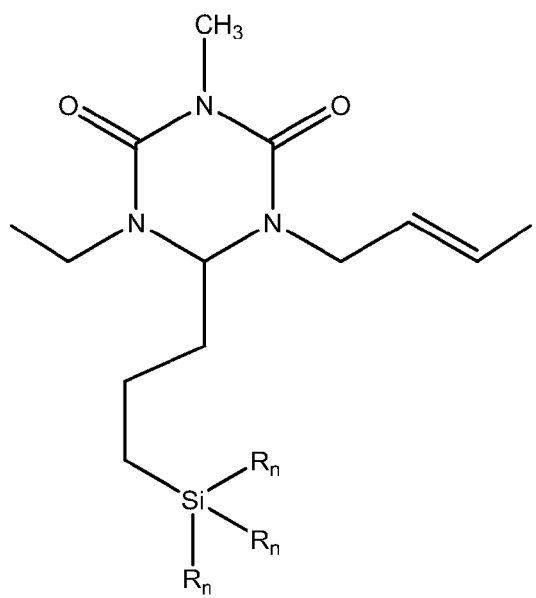
Figure 3C:
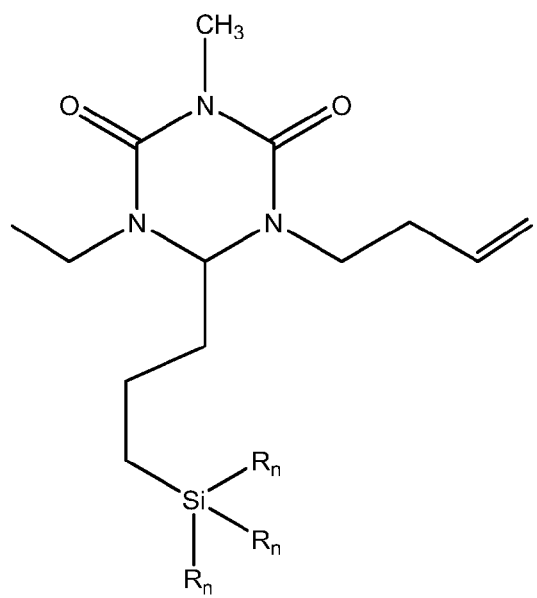
Figure 3D:
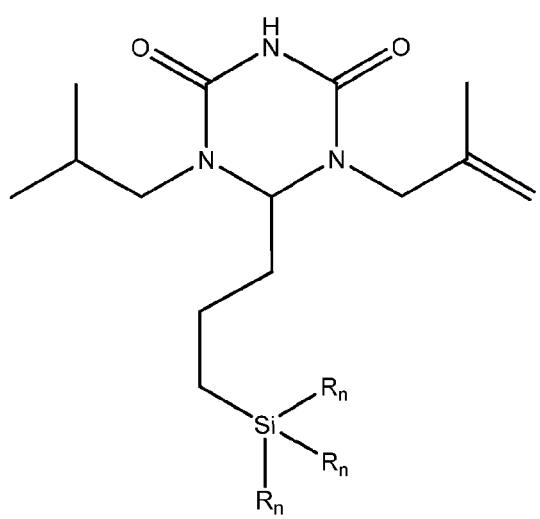
Figure 3D:
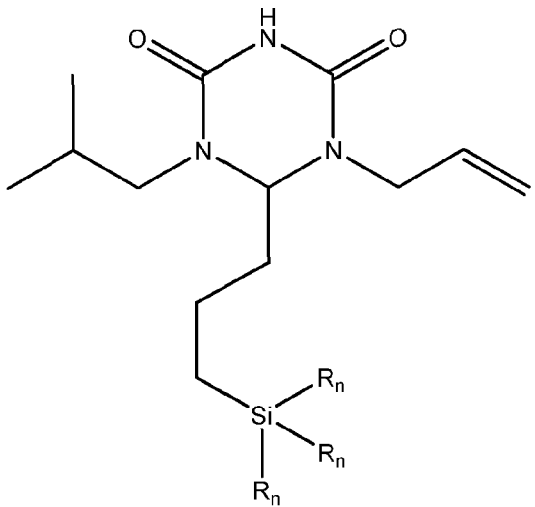
Figure 3D:
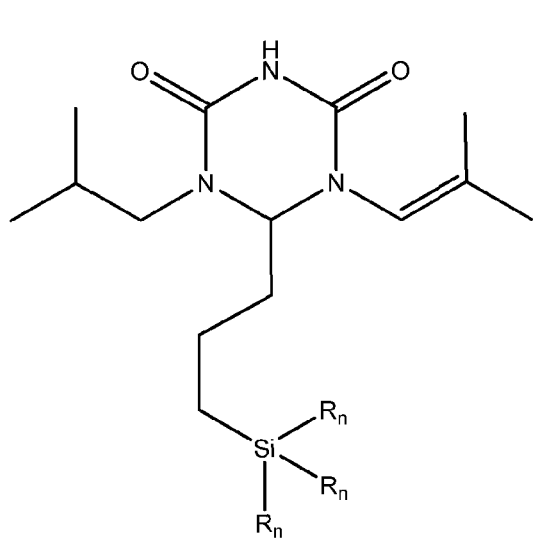
Figure 3D:
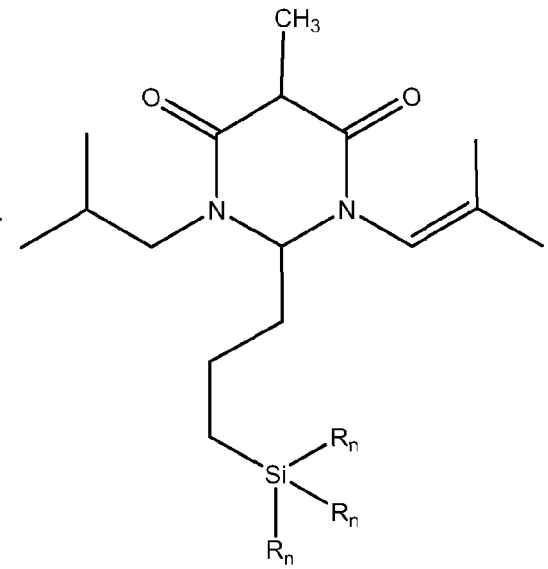

In one embodiment, the silane coupling agents have a general structure as shown in formula (I):

where Q comprises one or more groups that can provide covalent attachment to the polymer and Z comprises one or more groups that can provide covalent attachment to the filler. This arrangement is shown schematically in the drawing in FIG. 1A. In some examples, Q may include multiple attachment sites such that more than one polymer chain may be covalently bound to Q. A schematic of this arrangement is shown in FIG. 1B. In FIG. 1B, the two polymer chains may be the same or may be different. The sum of m+n is typically equal to four, with each of m and n independently selected from zero, 1, 2, 3, and 4. In some examples, n is 3 and Q is 1 or n is 2 and Q is 2 or n is 1 and Q is 3. It is also possible for n to be 4 and Q to be zero or for n to be zero and Q to be 4 depending on the exact substituents selected for Q and Z. FIG. 1C is similar to FIG. 1A except the polymer is a halopolymer such as, for example, a polymer including one or more fluorine, chlorine or bromine substituents. In FIG. 1D, the polymer is shown as a fluoropolymer such as, for example, those described herein.

In certain embodiments, the Z group of formula (I) may be selected such that reaction with one or more groups on the filler surface results in covalent bond formation between the coupling agent and the filler. In certain examples, Z may be a hydrolyzable group including, but not limited to, a hydroxy, an alkoxy, an acyl-oxyl, a halogen, an amine or other suitable hydrolyzable group. In some examples, the Z group(s) may be labile and cleaved or otherwise removed through dehydration or other suitable mechanisms such that the Si group of formula (I) can covalently bond to a surface moiety on the filler to covalently couple the silane to the filler. For example, Z may be a hydroxyl group that can protonate and leave as water with subsequent or concurrent formation of a covalent bond between the filler and the coupling agent. In some examples, Z may be an alkyl group comprising a hydroxyl group including, but not limited to, methoxy, ethoxy, propoxy, butanoxy or other oxygen containing alkyl groups which may be saturated or unsaturated. In addition, where more than one Z group is present, the Z group may be the same or may be different.

In some examples, the Q group or groups may be selected to include at least one site of unsaturation such that reaction with the polymer may occur. In certain instances, as discussed further below, the Q group may react with the polymer by a free radical mechanism to couple the polymer to the silane coupling agent and the filler. Illustrative Q groups are described and shown below. In certain embodiments, Q may include two or more sites of unsaturation such that more than one polymer chain may react with the coupling agent. In embodiments where more than one Q group is present, the Q groups may be the same or may be different. It is desirable that the Z group include one or more double bonds that can react by, for example, a free radical mechanism, with a polymer, e.g., a halopolymer such as, for example, a fluoropolymer.

In certain embodiments, the Q group may be selected to provide a compound having formula (II) below

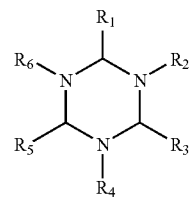

where either $R_1$ or $R_4$ comprises a group that attaches to the Si moiety of formula (I). In examples where $R_1$ comprises a group that attaches to the Si moiety of formula (I), $R_1$ may be C1-C6 alkyl (straight chain or branched), C1-C6 heteroalkyl (straight chain or branched), C1-C6 alkenyl (straight chain or branched), an ester group, a keto group, an ether group, phenyl or other suitable groups. In examples where $R_4$ comprises a group that attaches to the Si moiety of formula (I), $R_4$ may be C1-C6 alkyl (straight chain or branched), C1-C6 heteroalkyl (straight chain or branched), C1-C6 alkenyl (straight chain or branched), phenyl, an ester group, a keto group, an ether group or other suitable groups. The exact chain length of $R_1$ and $R_4$ may be selected to provide a desired spacing between the filler and the polymer. For example, it may be desirable to have a linking group L between the ring of formula (II) and the Si group of formula (I) such that steric hindrance between the polymer and filler can be reduced. Formulae (III) and (IV) show examples of this arrangement.

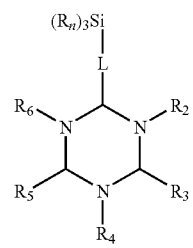

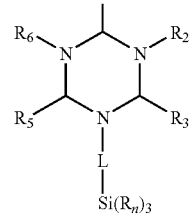

In formulae (III) and (IV), the linking group L may be C1-C6 alkyl (straight chain or branched), C1-C6 heteroalkyl (straight chain or branched), C1-C6 alkenyl (straight chain or branched), phenyl, an ester group, a keto group, an ether group or other suitable groups. In certain examples, the linking group may be methyl, ethyl, propyl, isopropyl, butyl, pentyl, hexyl or other hydrocarbons which may or may not include one or more heteroatoms such as, for example, nitrogen, oxygen and sulfur. In some examples, the linking group is an ether group having an oxygen moiety bonded directly to the ring structure of formula (II) with one or more other groups separating the oxygen moiety and the Si moiety. Illustrative specific coupling agents and linkers are described in more detail below. $R_n$ of formulae (III) and (IV) may be an alkoxy, an acyl-oxyl, a halogen, an amine or other suitable hydrolyzable group. The various $R_n$ groups may be the same or may be different.

In certain examples, $R_2$, $R_3$, $R_5$ and $R_6$ of formulae (II), (III) or (IV) may each by an alkyl group comprising two to six carbon atoms and having at least one unsaturated site, e.g., at least one double or triple bond and optionally a heteroatom, for example, sulfur, oxygen and nitrogen. In some examples, $R_2$ and $R_6$ may be the same, whereas in other examples $R_2$ and $R_6$ may be different. In certain examples, $R_3$ and $R_5$ may be the same, whereas in other examples $R_3$ and $R_5$ may be different. In some examples, $R_2$ and $R_6$ are each the same and $R_3$ and $R_5$ are each the same, with $R_2$ and $R_6$ being different from $R_3$ and $R_5$. For example, each of $R_3$ and $R_5$ may be oxygen to provide a keto group as shown in formulae (V) and (VI) below.

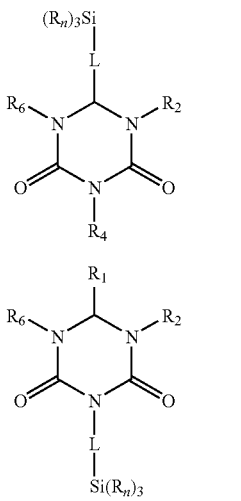

In certain examples, if $R_2$ and $R_6$ include sites of unsaturation, then $R_3$ and $R_5$ may be designed to have no sites of unsaturation. Similarly, if $R_3$ and $R_5$ include unsaturation sites, then $R_2$ and $R_6$ may be designed to have no unsaturation sites. In other examples, the unsaturation sites may be positioned on adjacent atoms of the cyclic structure, e.g., the unsaturation sites may be within $R_2$ and $R_3$ or $R_5$ and $R_6$. Other placement sites and arrangements of the unsaturation sites will be readily selected by the person of ordinary skill in the art, given the benefit of this disclosure.

In some examples of formula (V) and (VI), each of $R_2$ and $R_6$ may be C1-C6 alkenyl, which may be the same or may be different. Illustrative compounds are shown in FIGS. 2A-2D as formulae (VII)(a)-(VII)(p) where $R_n$ may be any of those groups listed herein, e.g., hydroxyl, methoxy, ethoxy, etc., or the specific groups shown in FIGS. 2A-2D. In addition, the site of unsaturation may be at a terminal carbon or between two internal carbons. The linking group L is shown in FIGS. 2A-2D as a propyl group (or an isopropyl group) but other groups are possible, as discussed below. In addition, partially or completely fluorinated derivatives of the structures shown in FIGS. 2A-2D are suitable compounds. In other examples of formulae (V) and (VI), one of $R_2$ and $R_6$ may be alkenyl. Illustrative compounds are shown in FIGS. 3A-3D as formulae (VIII)(a)-(VIII)(p). In addition, partially or completely fluorinated derivatives of the structures shown in FIGS. 3A-3D are also suitable compounds.

In certain embodiments of formulae (III) and (IV), each of $R_2$ and $R_6$ are absent to provide a compound as shown in formulae (IX) and (X) below

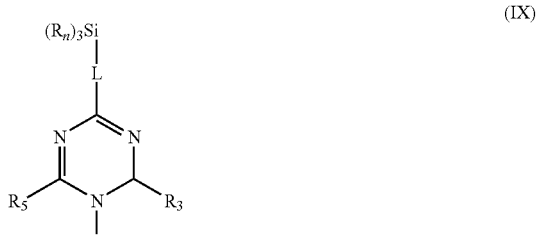

Figure 4A:
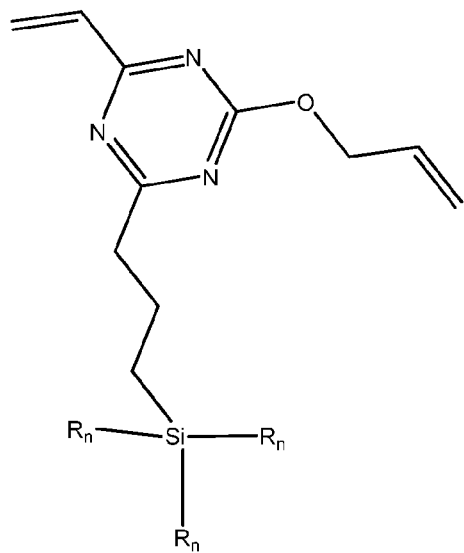
FIGS. 4A-4C show examples of formulae XI(a)-XI(I), in accordance with certain examples.
Figure 4A:
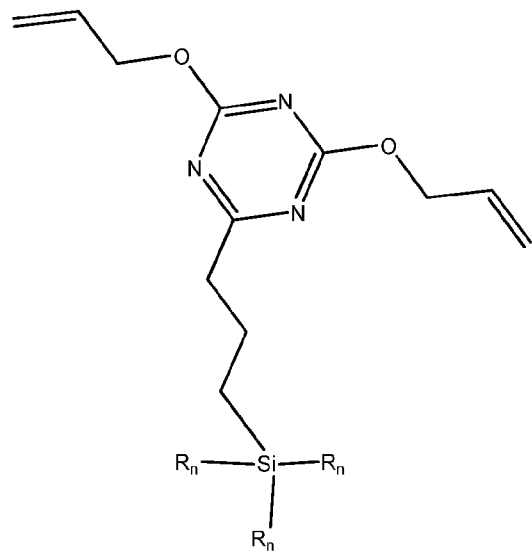
Figure 4A:
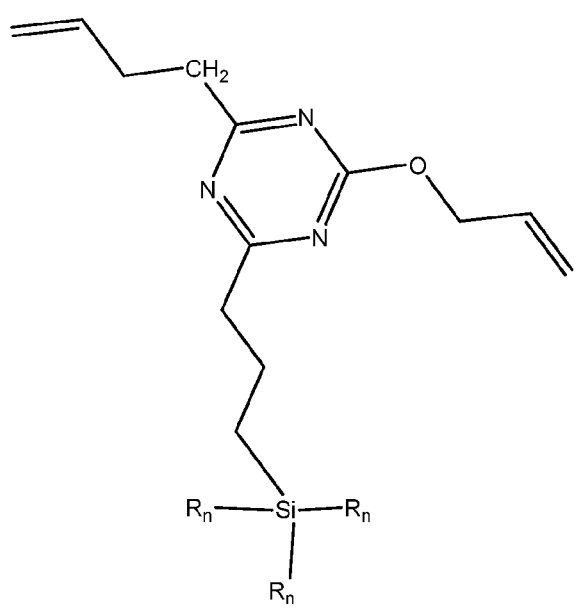
Figure 4A:
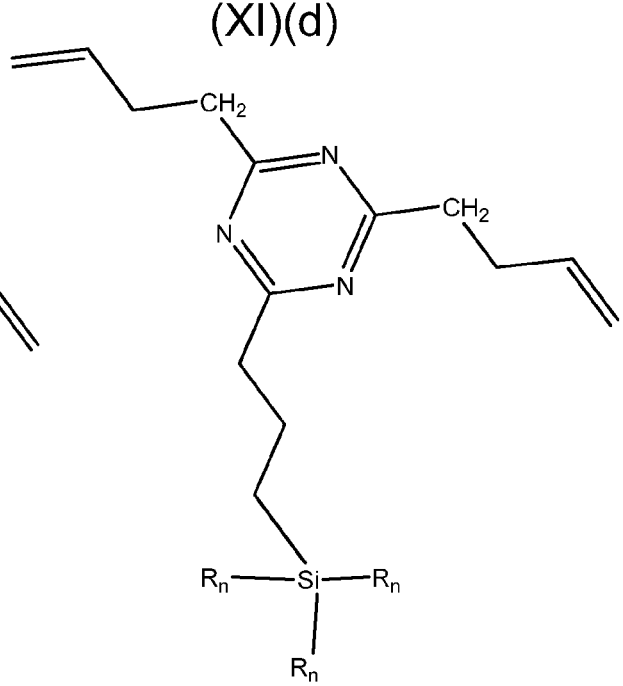
Figure 4B:
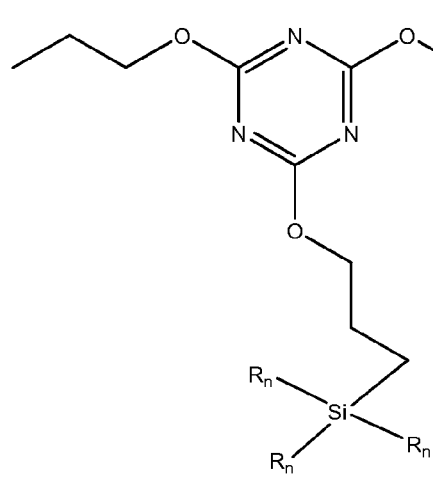
Figure 4B:
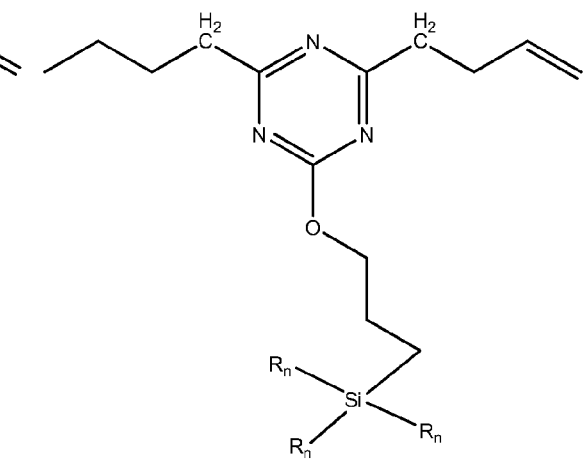
Figure 4B:
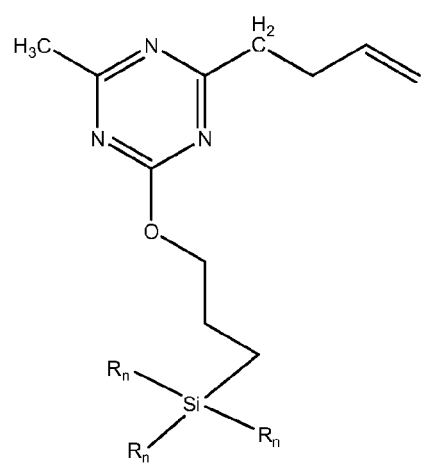
Figure 4B:
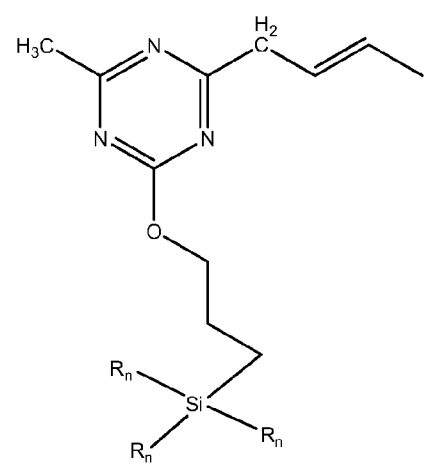
Figure 4C:
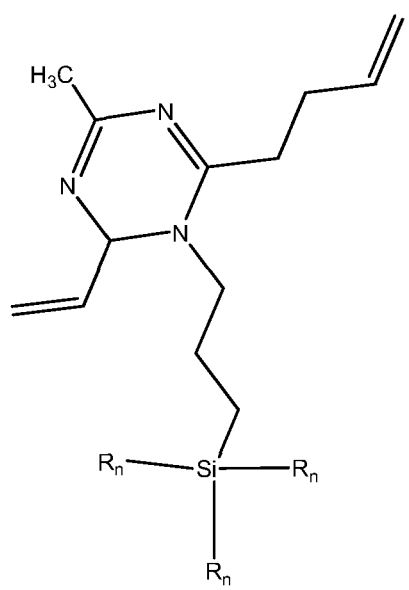
Figure 4C:
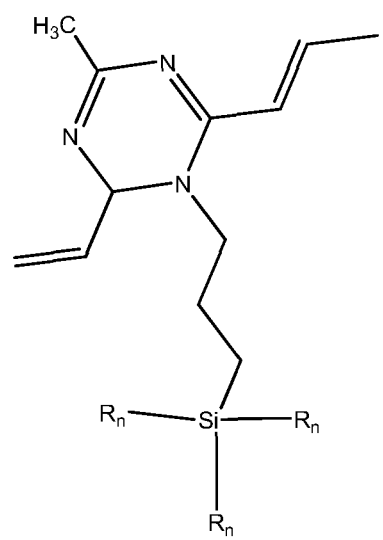
Figure 4C:
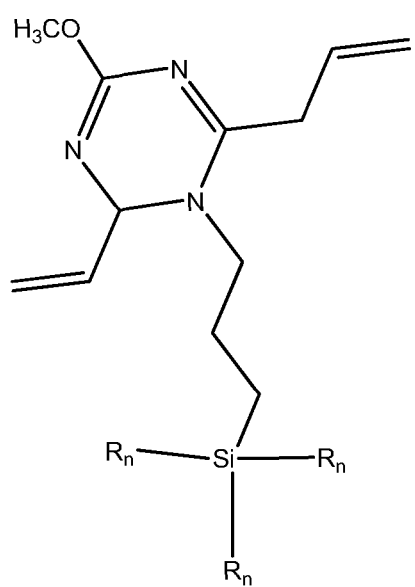
Figure 4C:
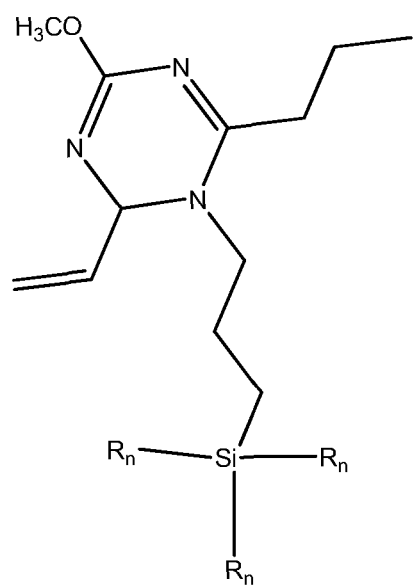

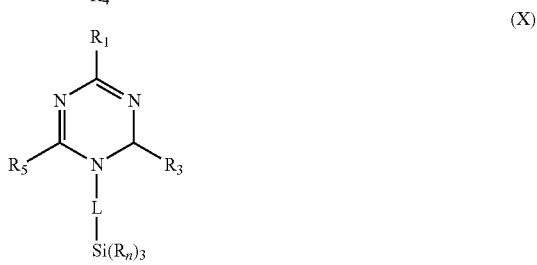

where $R_3$ and $R_5$ may each by an alkyl group comprising two to six carbon atoms and having at least one unsaturated site, e.g., at least one double or triple bond. L may be a linking group as described herein and $R_n$ may be a hydrolyzable group such, for example, as those described herein. Illustrative species of formulae (IX) and (X) are shown in FIGS. 4A-4C as formula (XI)(a)-(XI)(I). In some examples, each of $R_3$ and $R_5$ may be the same whereas in other examples, $R_3$ and $R_5$ may be different. In addition, partially or completely fluorinated derivatives of the structures shown in FIGS. 4A-4C are also suitable compounds.

In other embodiments, $R_4$ may be absent to provide a compound as shown in formula (XII) below.

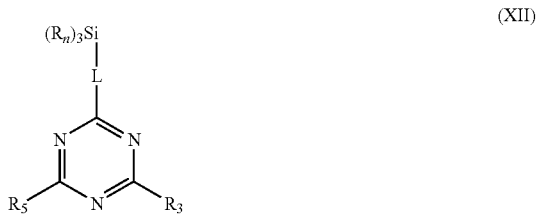

Figure 5:
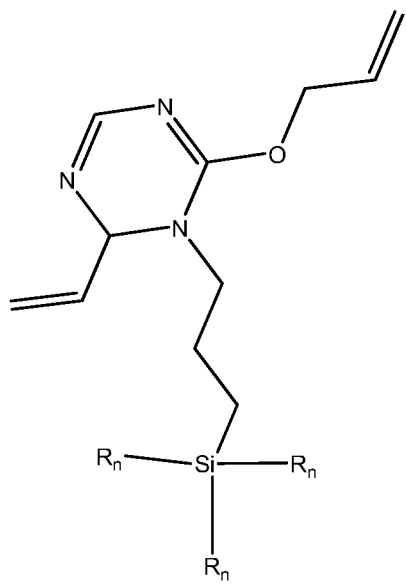
FIG. 5 shows examples of formulae XIII(a)-XIII(d), in accordance with certain examples.
Figure 5:
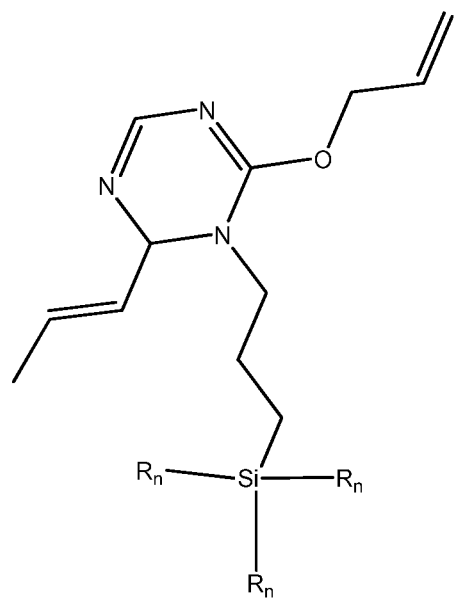
Figure 5:
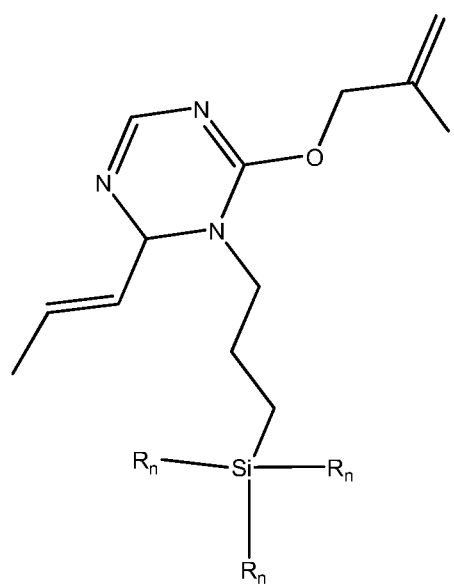
Figure 5:
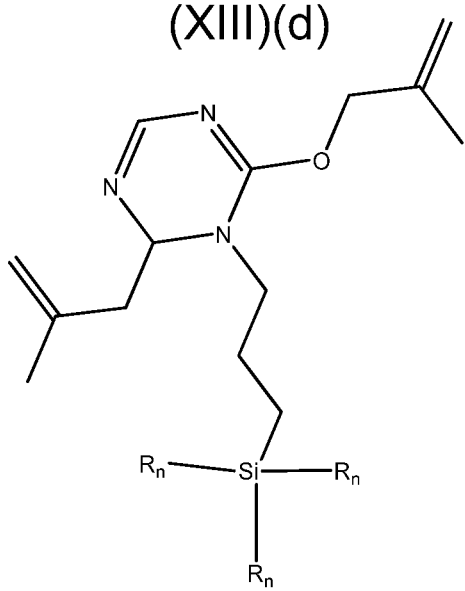

In formula (XII), $R_3$ and $R_5$ may each be an alkyl group, which may be the same or may be different, comprising two to six carbon atoms and having at least one unsaturated site, e.g., at least one double or triple bond. L may be a linking group as described herein and $R_n$ may be a hydrolyzable group such as, for example, those described herein. Illustrative species of formulae (XII) are shown in FIG. 5 as formula (XIII)(a)-(XIII)(d). In addition, partially or completely fluorinated derivatives of the structures shown in FIG. 5 are also suitable compounds.

The illustrative examples of the silane coupling agents described herein may be synthesized using known methods of producing silane compounds. For example, halo- or alkoxysilanes may be reacted with Grignard reagents (RMgX where R is an organic group and X is a halogen) or alkali metal organics, e.g., RLi where R is an organic group as shown in the reaction schemes below.

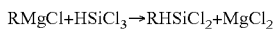

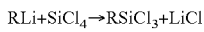

Another method of synthesizing silane coupling agents is through hydrosilylation of an olefin in the presence of a catalyst such as, for example, chrloroplastinic acid, t-butylperoxide and amine complexes. The silicon typically ends up on the least substituted carbon.

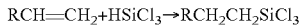

Hydrosilylation may occur, for example, in the presence of Karstedt catalyst ($Pt_2\{[(CH2=CH)Me_2Si]_2O\}_3$) to silylate an unsaturated side chain as shown, for example, in the reaction scheme below.

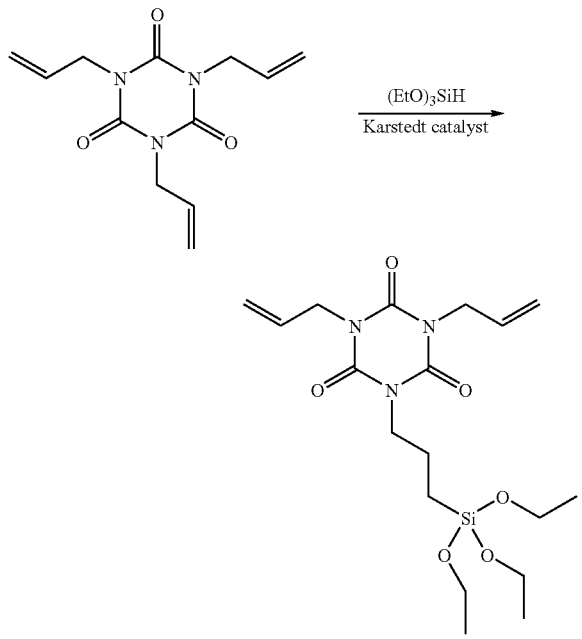

In other examples, organosilanes may also be produced by direct synthesis of an organohalide with silicon using heat and a copper catalyst.

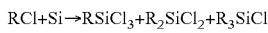

Figure 6A:
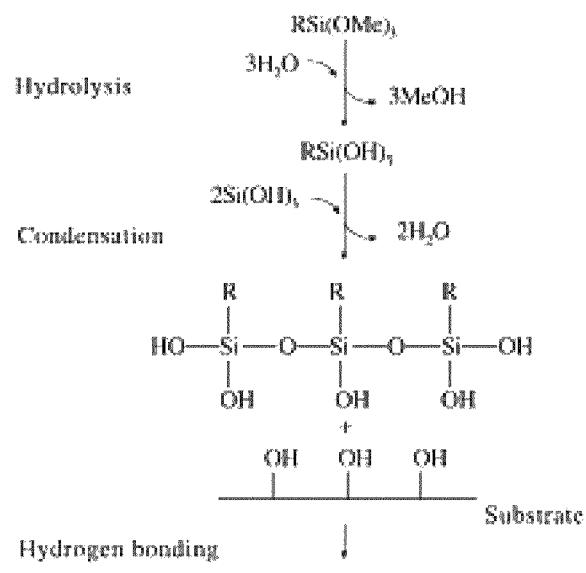
FIGS. 6A-6C show one process of covalently coupling a silane coupling agent to a surface of a filler, in accordance with certain examples.
Figure 6B:
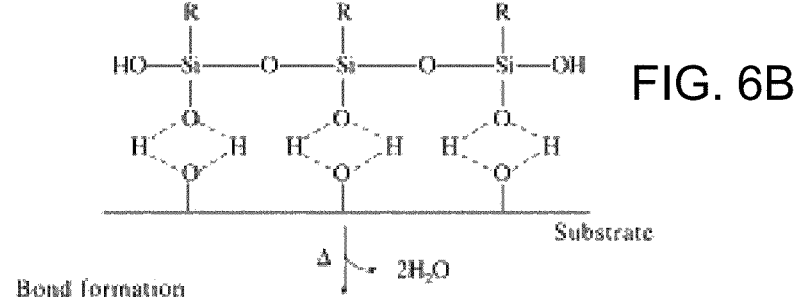
Figure 6C:
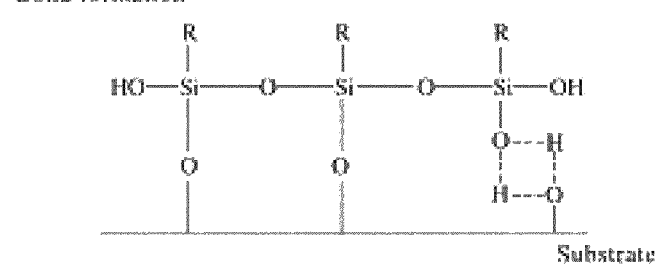

In certain embodiments, the silane coupling agents may react with the filler through various mechanisms. In one route, the silane may first react with additional silane coupling agents to provide a condensed product having polysiloxy linkages. Next, hydrogen bonding of the organo group(s) of the silane to the surface of the filler may first occur. Protons from the surface may be donated to the organo groups of the coupling agent followed by loss of water (dehydration) and subsequent linkage between the filler surface and the silane may then occur with loss of water. An illustration of the overall process is shown in FIG. 6 using a generic silane.

Illustrative organo groups that may be used in the silane coupling agents include, but are not limited to, —$SiCl_3$, —$SiBr_3$, —$SiF_3$, —$Si(OMe)_3$, —$Si(OEt)_3$, —$Si(OnPr)_3$, —$Si(OnBu)_3$, —$Si(OEtBu)_3$, and —$Si(OAc)_3$ where Me is methyl, Et is ethyl, nPr is n-proply, nBu is n-butyl, and Ac is acetyl. The substituents of the silane group need not be the same. In some examples, three of the substituents may be the same, two of the substituents may be the same or all three substituents may be different. It is desirable that all substituents of the silane be hydrolyzable groups whether or not all the substituents are the same or not.

Figure 7:
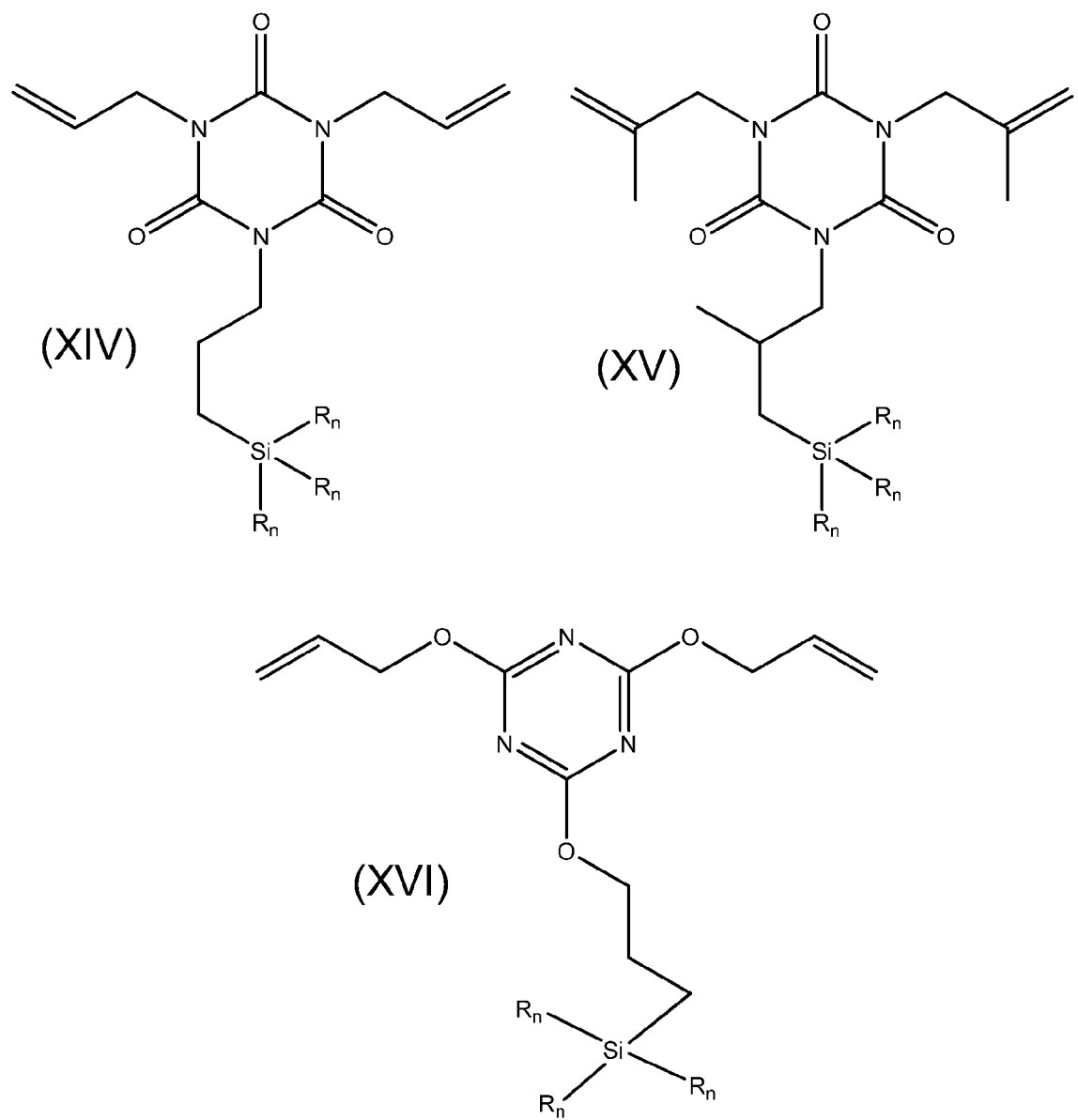
FIG. 7 shows structures of TAIC, TMAIC and TAC-silane coupling agents, in accordance with certain examples.
Figure 8A:
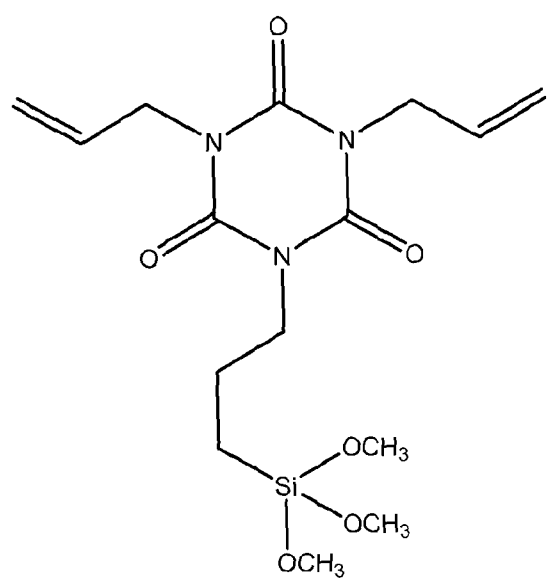
FIGS. 8A-8D show structure of specific TAIC-silane coupling agents, in accordance with certain examples.
Figure 8A:
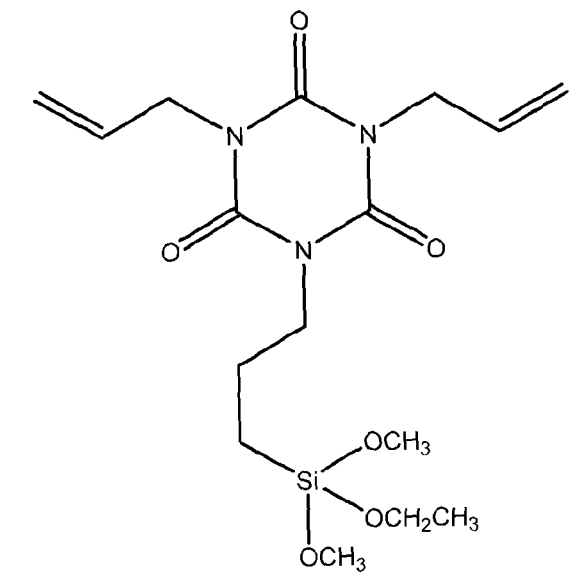
Figure 8A:
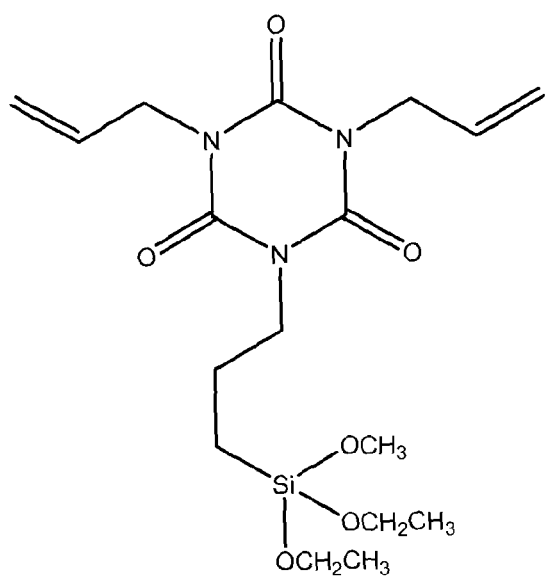
Figure 8A:
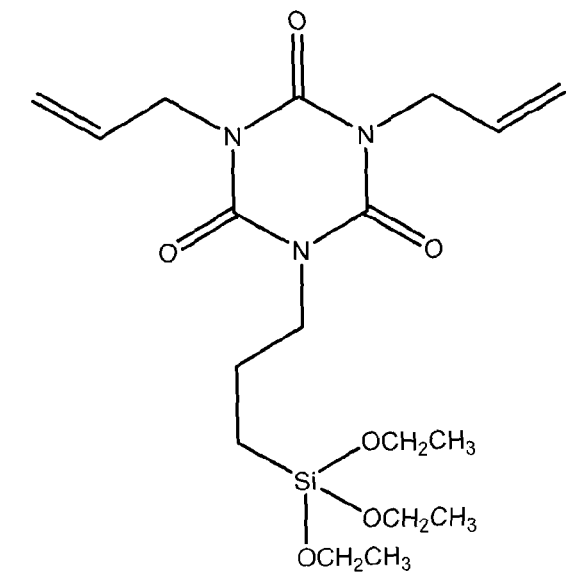
Figure 8B:
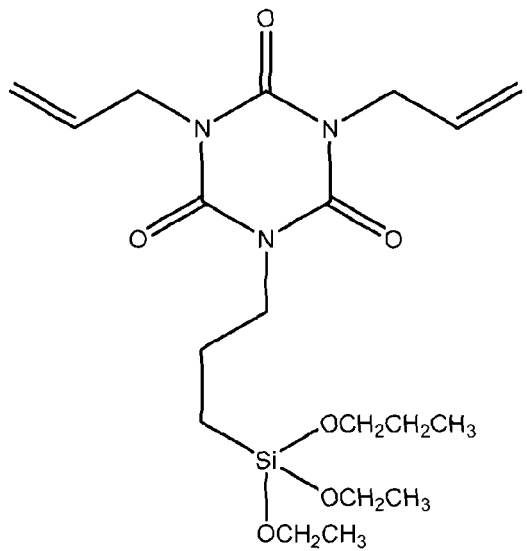
Figure 8B:
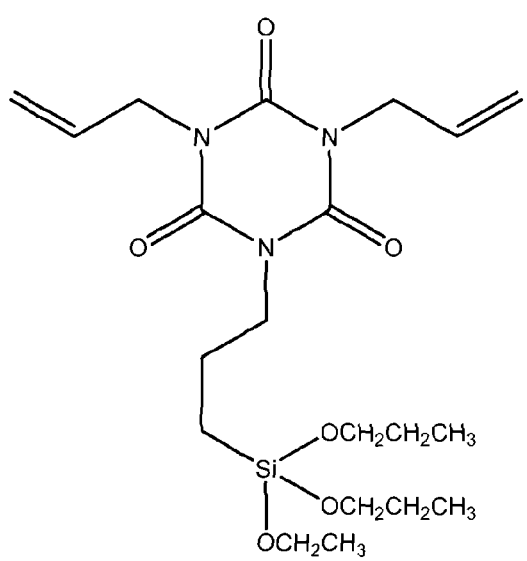
Figure 8B:
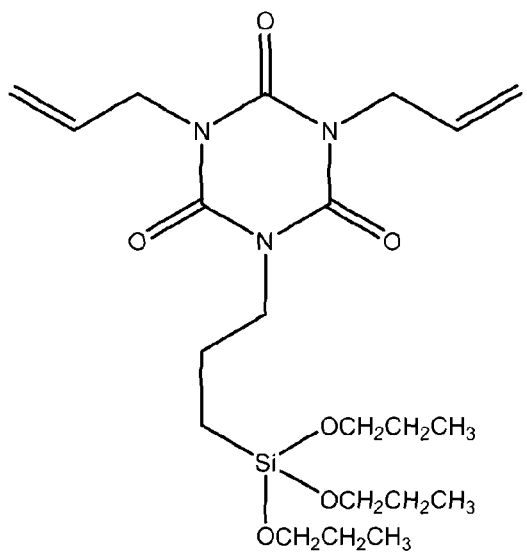
Figure 8B:
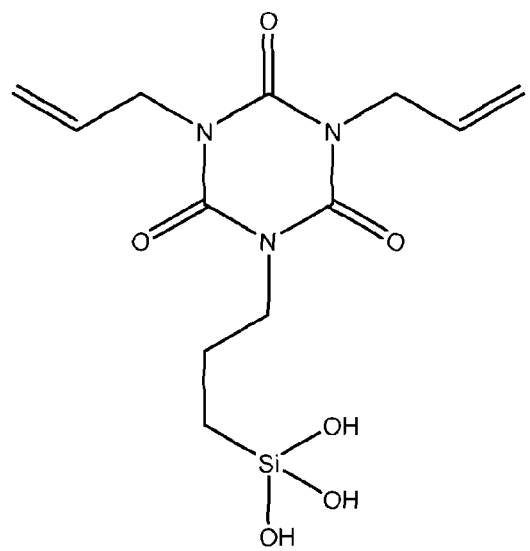
Figure 8C:
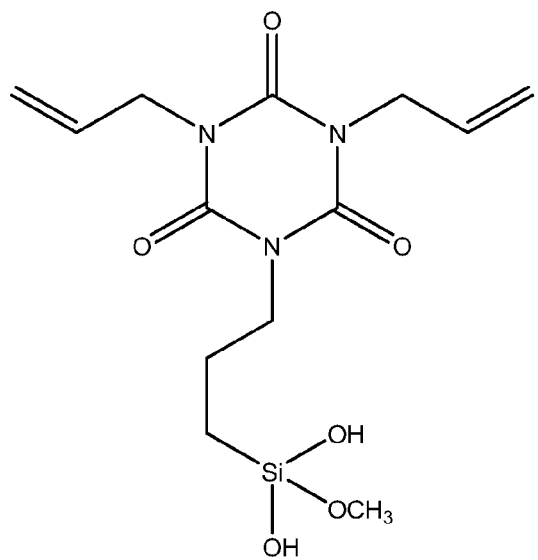
Figure 8C:
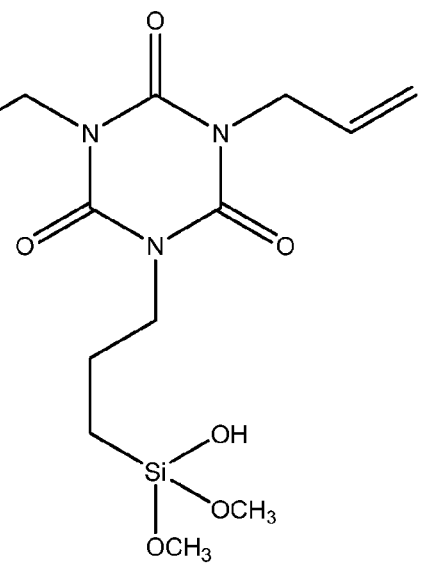
Figure 8C:
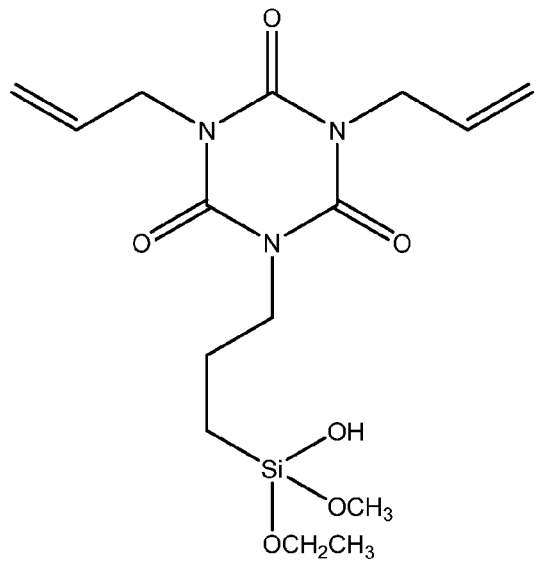
Figure 8C:
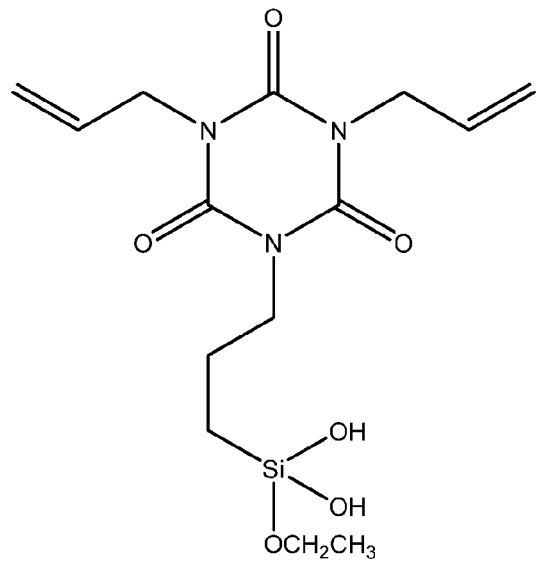
Figure 8D:
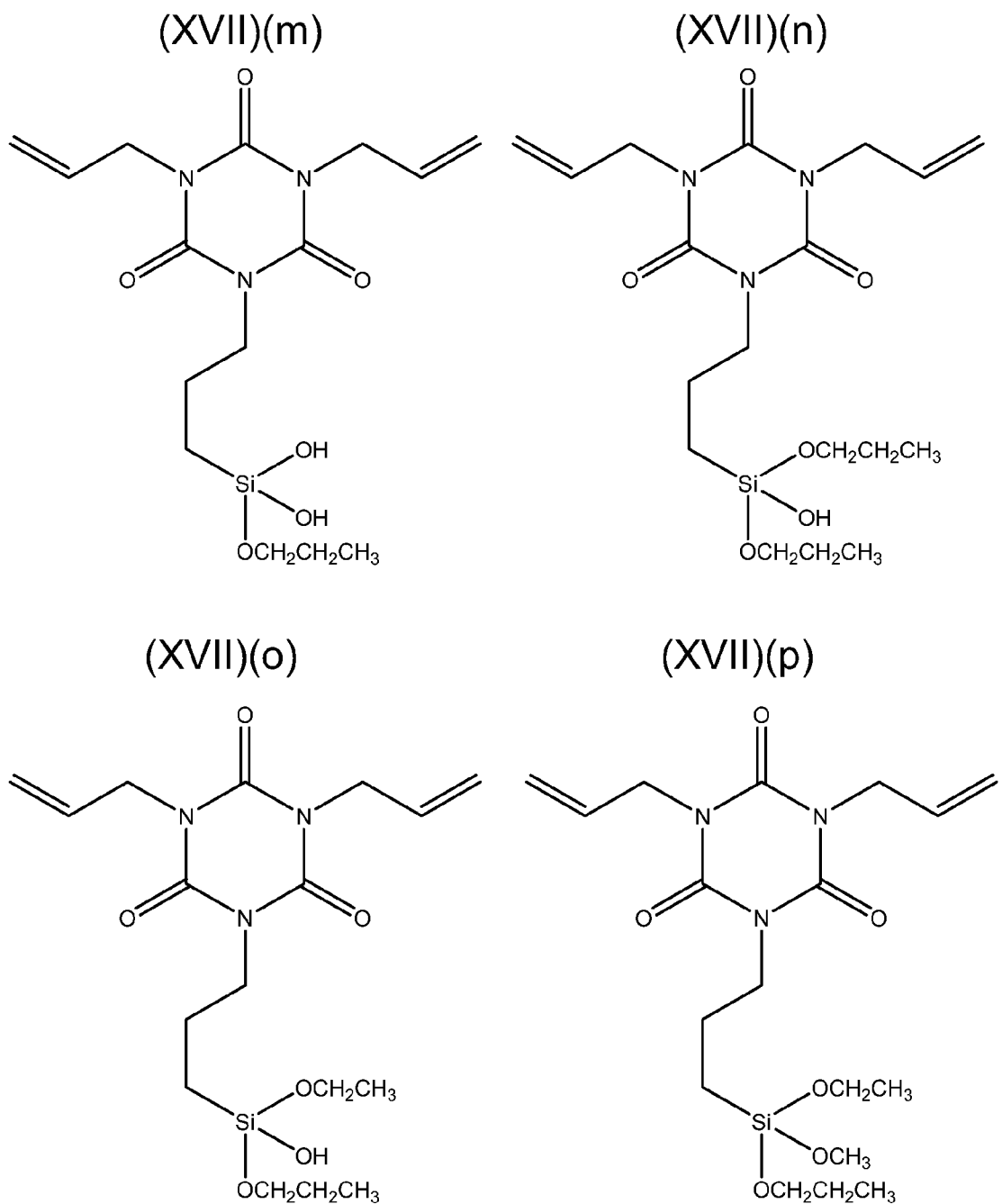
Figure 9A:
FIGS. 9A-9D show structure of specific TMAIC-silane coupling agents, in accordance with certain examples.
Figure 9A:
Figure 9A:
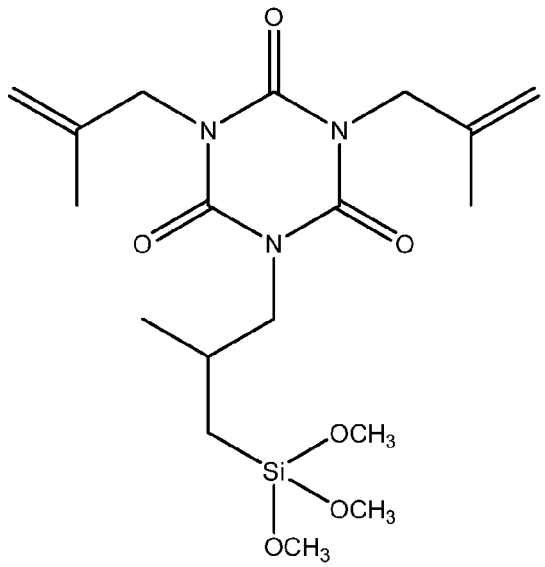
Figure 9A:
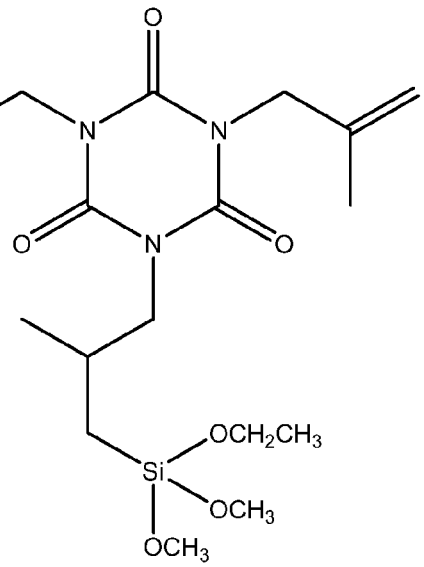
Figure 9A:
Figure 9A:
Figure 9A:
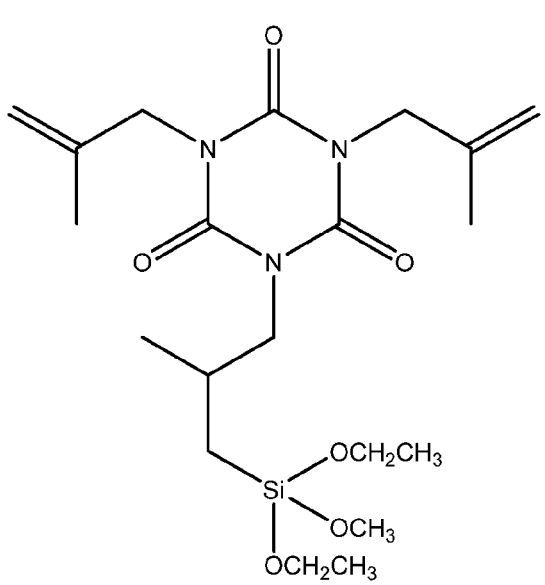
Figure 9A:
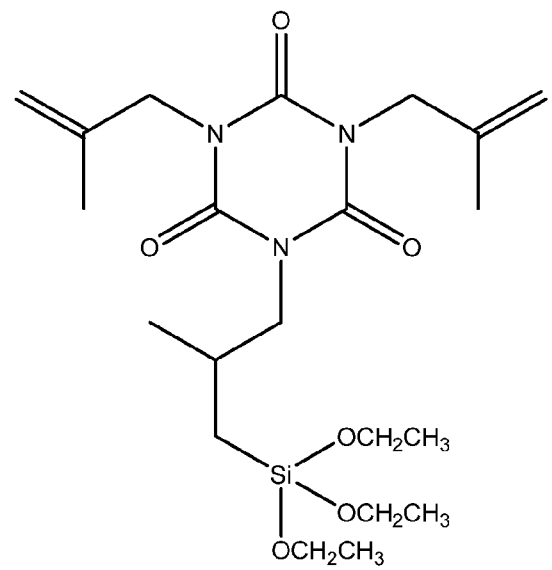
Figure 9B:
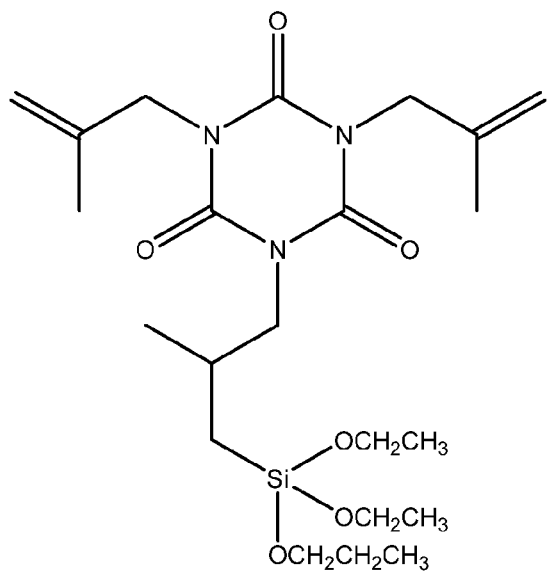
Figure 9B:
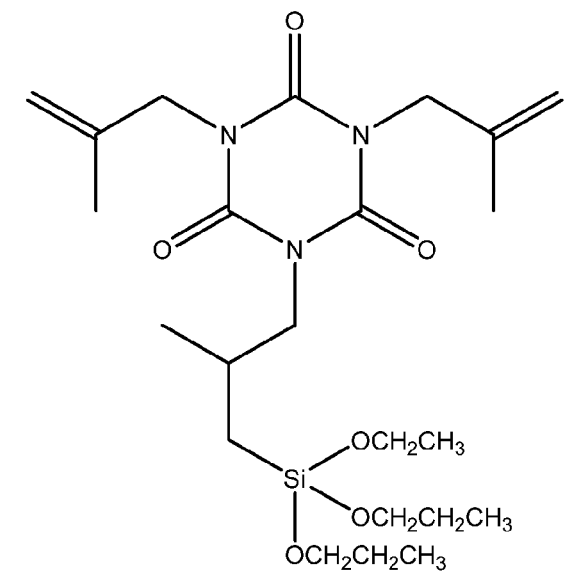
Figure 9B:
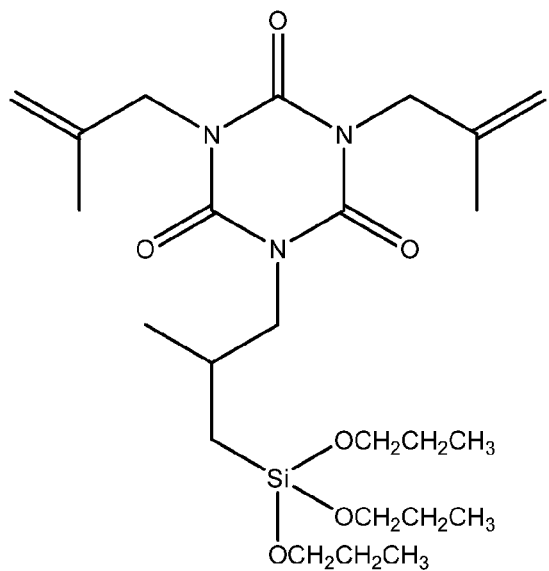
Figure 9B:
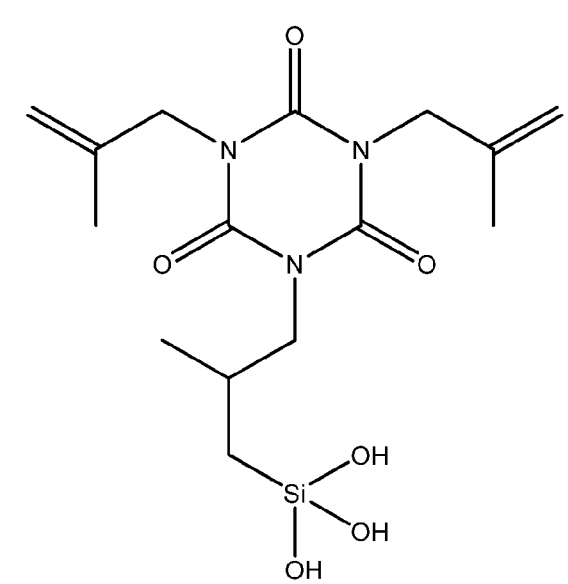
Figure 9C:
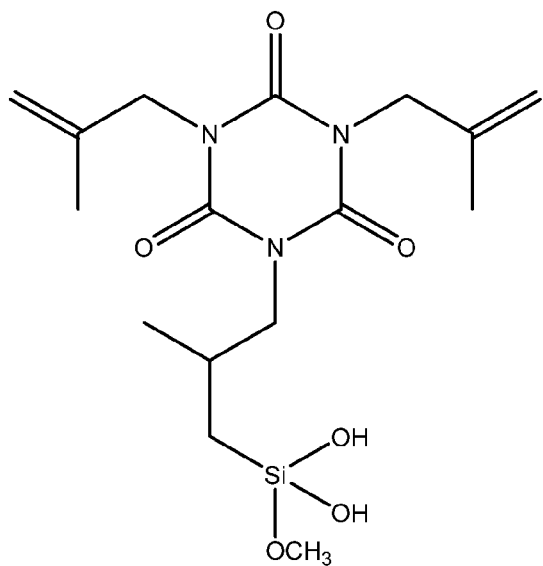
Figure 9C:
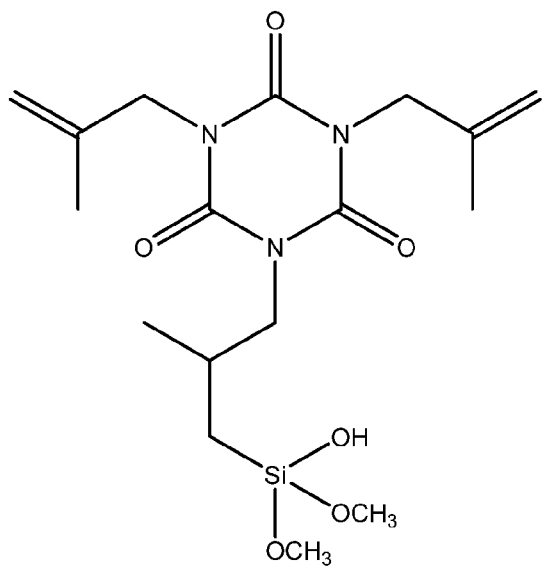
Figure 9C:
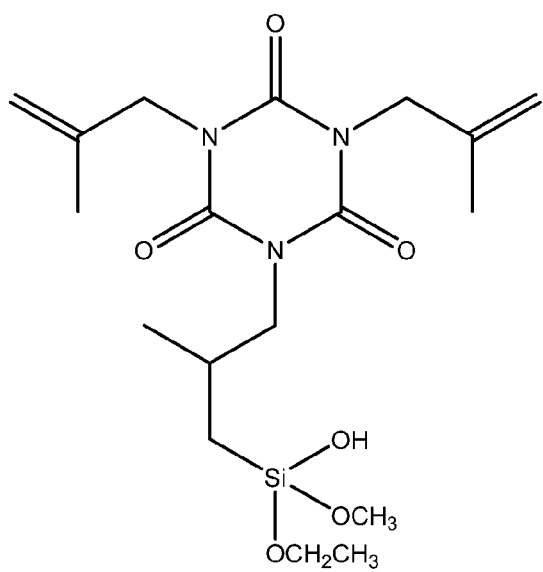
Figure 9C:
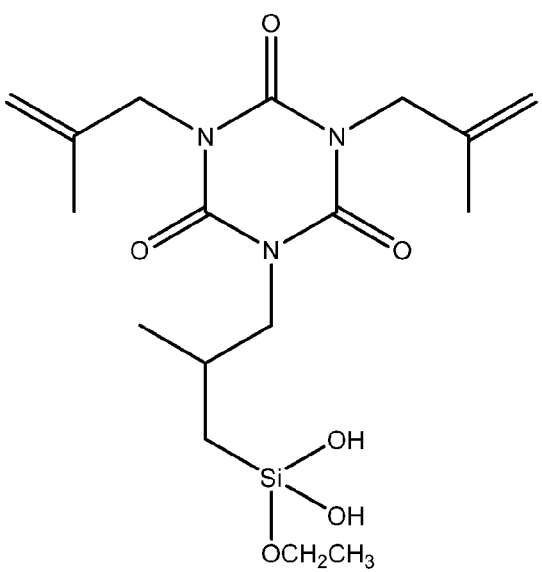
Figure 9D:
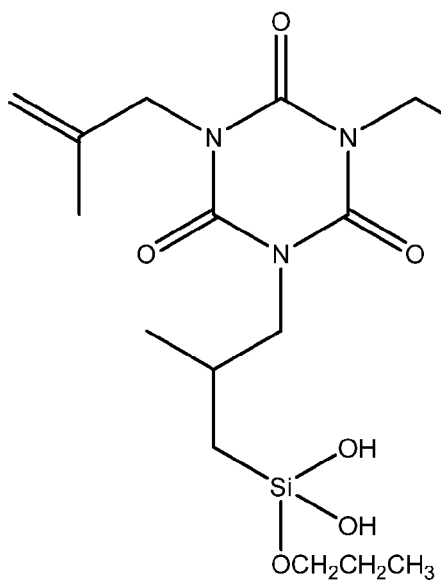
Figure 9D:
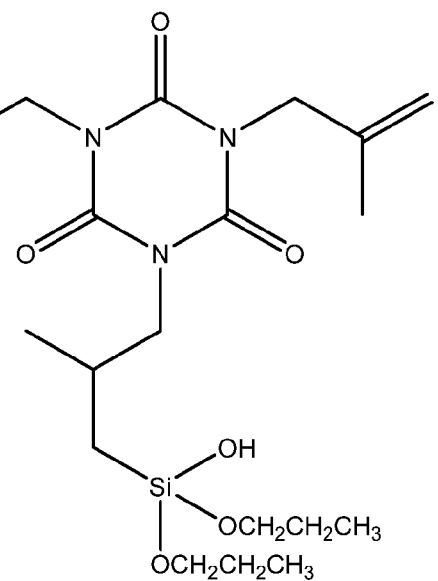
Figure 9D:
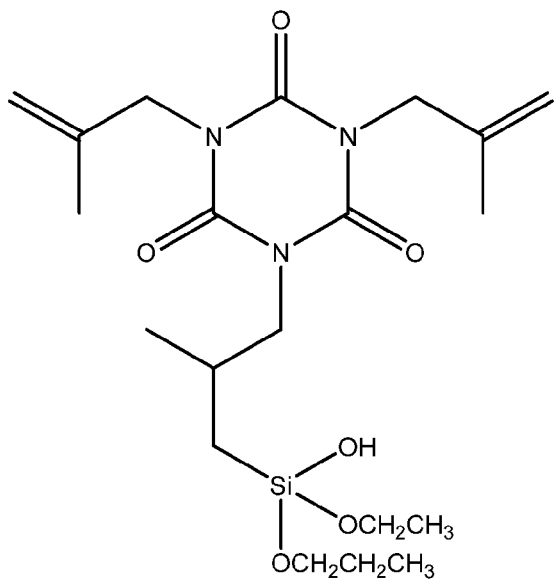
Figure 9D:
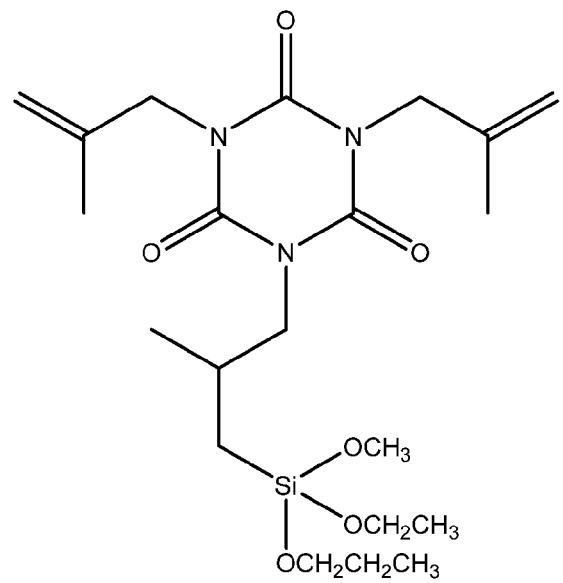
Figure 10A:
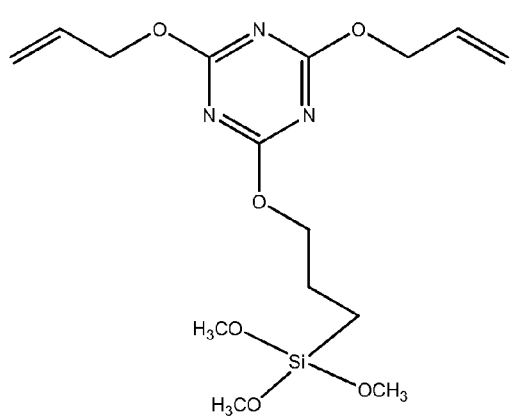
FIGS. 10A-10D show structure of specific TAC-silane coupling agents, in accordance with certain examples.
Figure 10A:
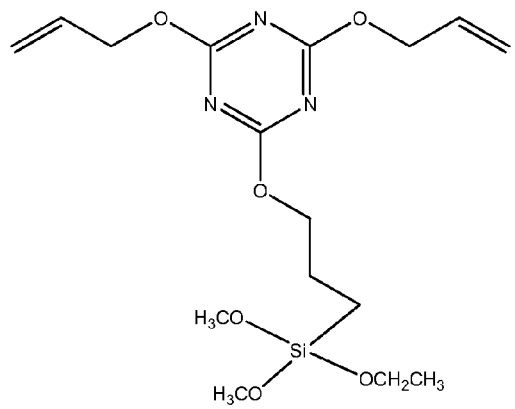
Figure 10A:
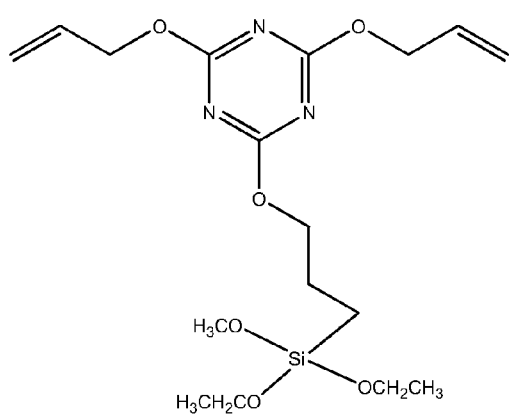
Figure 10A:
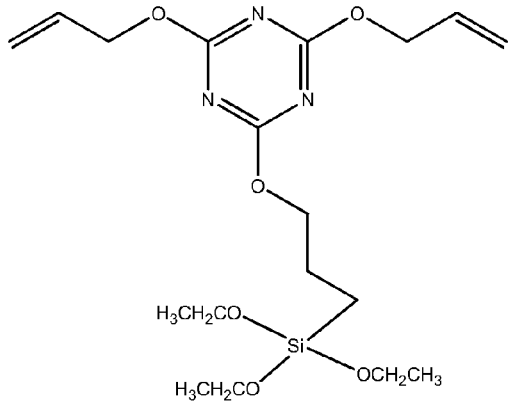
Figure 10B:
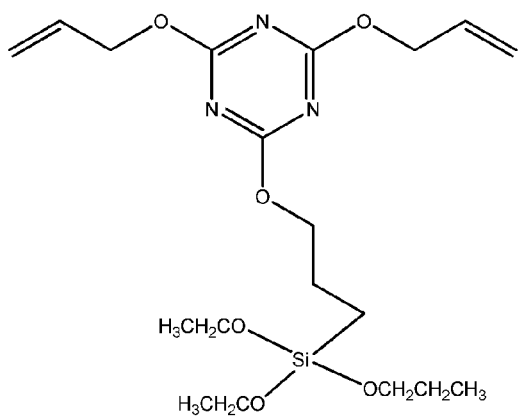
Figure 10B:
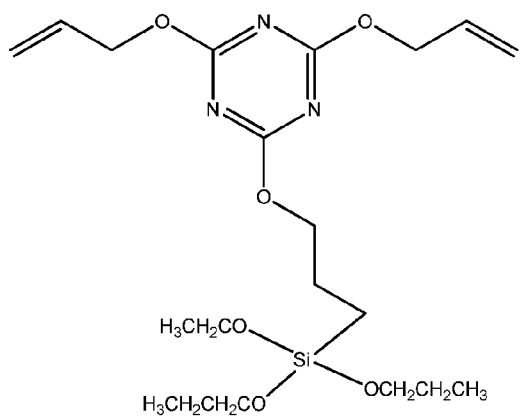
Figure 10B:
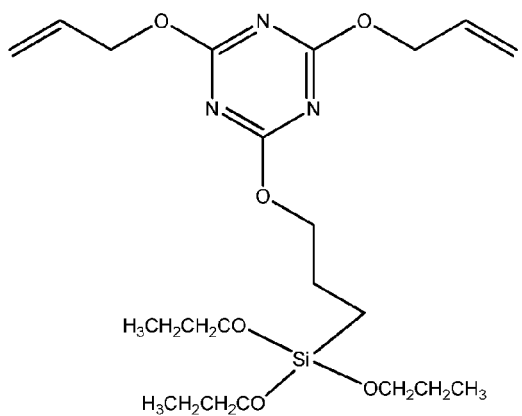
Figure 10B:
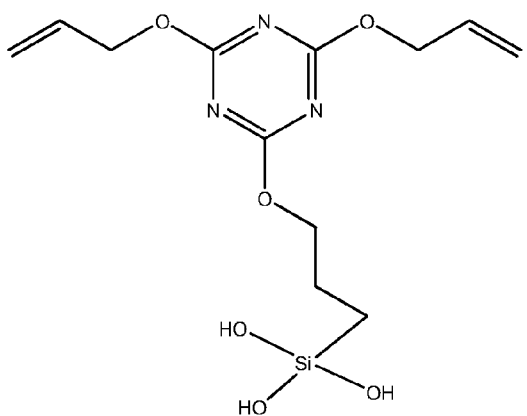
Figure 10C:
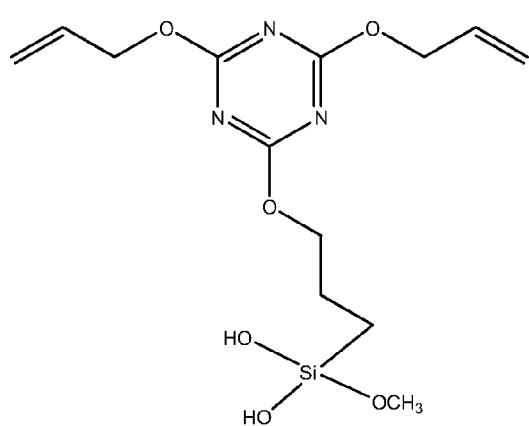
Figure 10C:
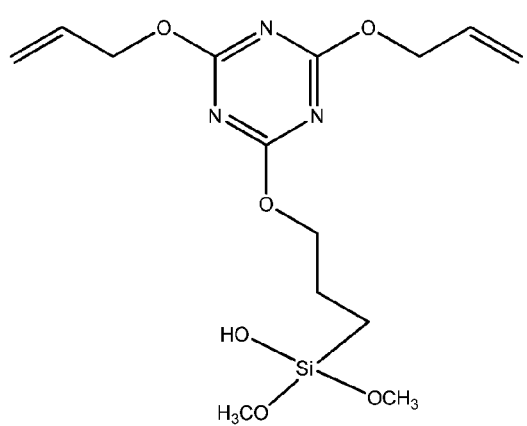
Figure 10C:
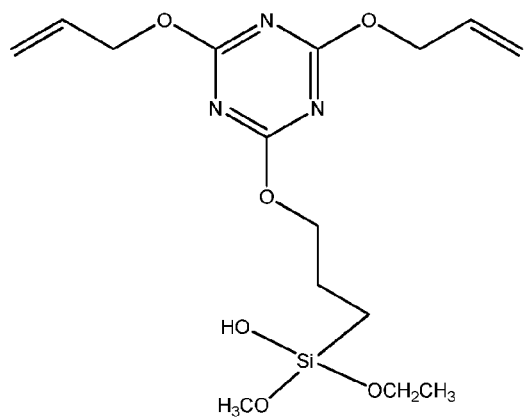
Figure 10C:
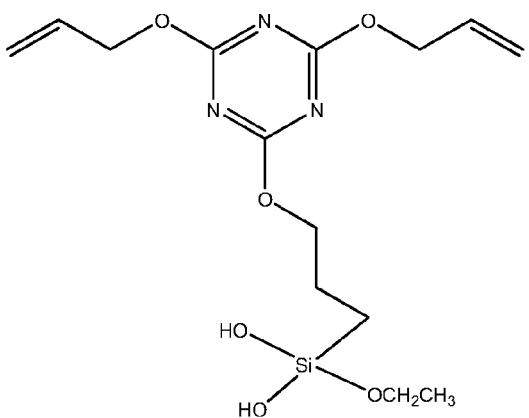
Figure 10D:
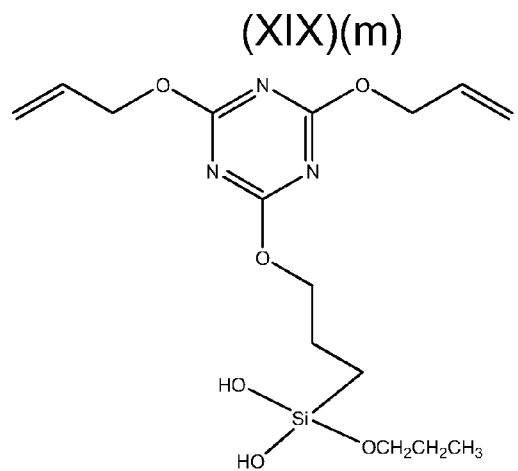
Figure 10D:
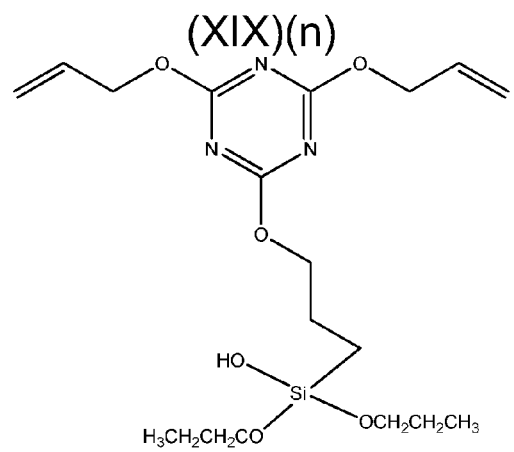
Figure 10D:
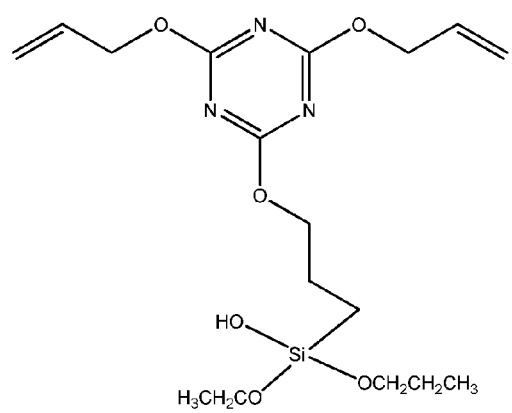
Figure 10D:
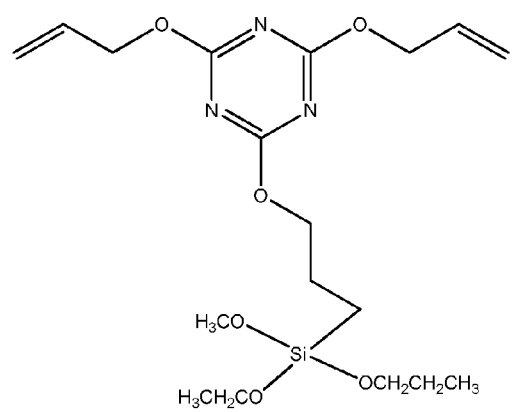

In certain embodiments, the silane coupling agent may take the form of a compound as shown in formulae (XIV), (XV) or (XVI) in FIG. 7, which are referred to herein in certain instances as TAIC-silane, TMAIC-silane and TAC-silane, respectively. Specific examples of TAIC-silanes are shown in FIGS. 8A-8D as formulae (XVII)(a)-(XVII)(p), specific examples of TMAIC-silanes are shown in FIGS. 9A-9D as formulae (XVIII)(a)-(XVIII)(p), and specific examples of TAC-silanes are shown in FIGS. 10A-10D as formulae (XVIIII)(a)-(XVIIII)(p). While the linking group of FIGS. 8-10 is a propyl group or an isopropyl group, other linking groups are possible as described herein. The reactivity of the two vinyl groups within the compounds shown in formulae (XIV)-(XVIII)(p) is substantially identical, and the good thermal resistance of TAIC-silanes, TMAIC-silanes and TAC-silanes permits them for use in high application temperature commonly used with fluoroelastomers. TAIC-silanes in particular can provide improved properties due to a good balance of cure rates, cure states and thermal stability. In addition, partially or completely fluorinated derivatives of the structures shown in FIGS. 7-10 are suitable compounds.

In certain embodiments, to synthesize the compounds of formulae (XIII)-XVIII(p), the base structure may be hydrosilylated, e.g., TAIC, TMAIC or TAC base structure can be hydrosilylated. For example, hydrosilylation of TAIC, TMAIC, and TAC with proper tri-functional (triethoxy, trimethoxy, or trichloro) silanes at the presence of Karstedt catalyst can provide the silane coupling agents. As an example, one synthesis route of TAIC-silane is shown in the text above using triethoxysilyl group and Karstedt catalyst.

In certain examples, to improve further the thermal stability of the silane coupling agents, structure modifications include: (1) changing the linker structure to include one or more halides. For example, a propyl linker may be switched to a perfluorinated propyl linker (—$CH_2$—$CH_2$—$CH_2$— to —$CF_2$—$CF_2$—$CF_2$—); (2) changing the linker to thermally stable aromatics such as phenyl and biphenyl structures; (3) attaching the coupling agent to dipodal silane. In addition, the length of the linker can also be varied to achieve the best mobility of the reactive vinyl groups without sacrificing too much on the thermal stability. In general, better stability can be observed using shorter linkers, e.g., ethyl or propyl linkers, than using longer linkers. Examples of such changes are shown in the linking group species illustrated in FIG. 11 with the wavy lines representing attachment sites to other portions of the silane coupling agent. Illustrative linkers include those having one to six carbon atoms (straight chain or branched), phenyl groups, biphenyl groups, fluoro groups or other substituents discussed herein.

In certain embodiments, by modifying the filler surface, different properties are achieved. First, the surface polarity of the silica filler is dramatically changed. For example, before silanization, silica fillers (fumed or precipitated) have very high surface energy. They tend to form large agglomerates in a polymer matrix which often become the crack-initiation sites and thus degrade the mechanical properties of the composites. When silica fillers are treated with silane coupling agents, their surface energy is lowered significantly and it becomes similar to that of fluoroelastomers. These modified fillers will absorb much less moisture, or even not absorb water vapor at all if complete silane coverage is achieved. As a result, the fillers will disperse very well in fluoroelastomers when compounded with fluoroelastomer gums. Second, the silanes are reactive. At the curing conditions of fluoroelastomers and etc., the vinyl groups of these silanes will react (leading to cross-links at the filler surfaces) with the functional groups on the polymers and thus bind the fillers covalently to the polymers. For example, there may be covalently bound rubber on the filler surfaces. The bound rubber can be critical for mechanical properties of rubbers.

When comparing bound rubber content and properties in different systems or at different conditions for one particular polymer-filler system, several factors should be considered as bound rubber is sensitive to the chemical and physical nature of the polymers and fillers, as well as the experimental conditions (temperature, solvent and etc.) at which the bound rubber is isolated and measured. Covalent bound rubber obtained using the silane coupling agents described herein is very different from that in polyolefin-carbon black systems where physical attractions tether the polymer layer near the filler surfaces. The bond dissociation energies of silicon-oxygen, silicon-carbon and carbon-carbon (single) bonds, which are the major types of chemical bonds at the TAIC-silane series modified silica surface, are about 370-570 kJ/mol. As a comparison, the absorption energy of polyolefins on carbon blacks is typically about 10-35 kJ/mol (at least one order of magnitude weaker). The exceptionally strong bonding present in the covalently bound rubber can assist in providing excellent high-temperature resistance of the polymer compounds.

Figure 11:
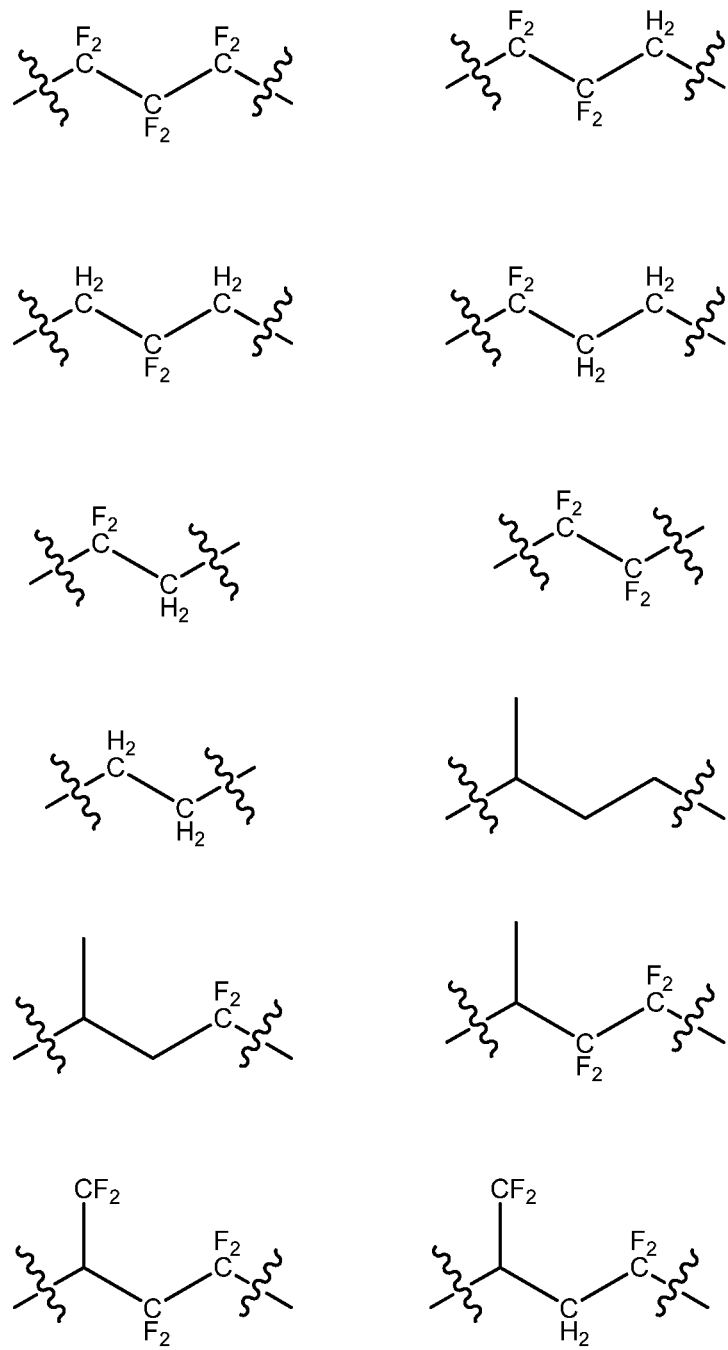
FIG. 11 show structures of silane coupling agents having different linking groups, in accordance with certain examples.
Figure 12:
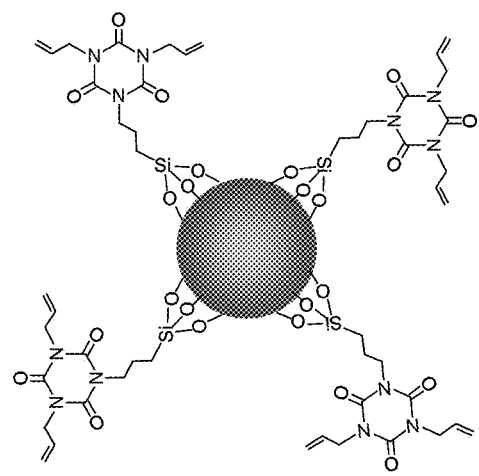
FIG. 12 is an illustration of a filler particle covalently coupled to a silane coupling agent, in accordance with certain examples.

In certain embodiments, the surface modification of silicate surfaces using these silane coupling agents can be carried out by standard procedures. The coupling agents can be applied to the substrates by deposition from aqueous alcohol, deposition from aqueous solution, bulk deposition onto powders by a spray-on method, integral blend method, anhydrous liquid phase deposition, vapor phase deposition, spin-on deposition and spray application. For chlorosilanes, they can be deposited from alcohol solution. Notwithstanding which particular application procedure may be selected, the reaction of the silane coupling agents can be categorized into four steps for convenience purposes. First, hydrolysis of the three hydrolyzable groups occurs (water is present in the solvent or absorbed at the surface from air). Condensation to oligomers follows. The oligomers then form hydrogen bonds with hydroxyl group on the surface. Finally, during drying or curing, a covalent linkage is formed with the substrate with concomitant loss of water. One example of the hydrolytic deposition of silanes is shown in FIG. 6. An illustration showing a TAIC-silane covalently coupled to the surface of a silica particle is shown in FIG. 12. In use, the silica filler is rarely present as a single spherical particle as shown in FIG. 11. In many instances, the silica fillers arrange themselves similar to strings of pearls.

In certain embodiments, an excess of silane coupling agent may be used such that substantially all accessible hydroxyl sites (or other reactive sites) on the filler surface can be modified with a silane coupling agent. In other examples, complete coverage with silane coupling agents is not necessary. High-temperature silanes such as phenyltriethoxysilane, pentafluorophenyltriethoxysilane, p-tolyltrimethoxysilane, p-trifluoromethyltetrafluorophenyl-triethoxysilane and etc. can be mixed with the silane coupling agents to dilute the surface concentration of the coupling silanes. These high-temperature silanes serve as covering agents which only modify the surface polarity of the fillers and do not form covalent bonds to any substantial degree.

In certain examples, the exact filler used with the silane coupling agents is not critical. In particular many different types of fillers may be used, and in certain instances more than one type of filler may be used. Illustrative types of fillers that can be used include, but are not limited to, silica, precipitated silica, amorphous silica, vitreous silica, fumed silica, fused silica, quartz, glass, aluminum, aluminum-silicate (e.g., clays), copper, tin, talc, inorganic oxides (e.g. $Al_2O_3$, $Fe_2O_3$, $TiO_2$, $Cr_2O_3$), steel, iron, asbestos, nickel, zinc, silver, lead, marble, chalk, gypsum, barites, graphite, carbon black, treated carbon black such as, for example, silicon treated carbon black and other particles, powders and materials that include, or can be chemically modified to include, one or more surface reactive groups.

Similar to the fillers, the exact polymer used with the silane coupling agents may vary. In one embodiment, polymers that include one or more of a double bond, halogen, leaving groups or that can react by free radical mechanisms may be used with the silane coupling agents described herein. Illustrative polymers include, but are not limited to a high density polyethylene, a nylon, a polycarbonate, a polyether sulfone, a polyphenylene oxide, a polyphenylene sulfide, a polypropylene, a polystyrene, a polyurethane, a polysulfone, a polyvinylchloride, a polyamide, a polyimide, a polyamide-imide, a polybutylene, a polybutylene terphthalate, a polyepoxide and other polymers. In some examples, a single type of polymer, different polymers, blends of polymers and the like may be used. Thus, in examples described herein that use a fluoropolymer in combination with a coupling agent, the fluoropolymer may be substituted with, or used in combination with, one or more other polymers.

In one embodiment, a halopolymer such as a fluoropolymer, a chloropolymer, and a bromopolymer may be used. Mixed halo polymers including two or more different halo substituents, such as, for example, chlorofluoropolymers and bromofluoropolymers, may also be used. Halopolymers may also include heteroatoms including, but not limited to, nitrogen, oxygen, sulfur and heterogroups formed from nitrogen, oxygen and sulfur. Of particular interest for use with the cross-linkers disclosed herein are fluoropolymers, which are difficult to cross-link due to the inertness of the carbon-fluorine bond. Fluoroelastomers are typically synthesized by radical co-, ternary or tetrapolymerizations of fluoroalkenes. Examples of fluoroelastomers include copolymers comprising units of vinylidene fluoride (VDF or $VF_2$) and units of at least one other copolymerizable fluorine-containing major monomer such as tetrafluoroethylene (TFE), hexafluoropropylene (HFP), chlorotrifluoroethylene (CTFE), vinyl fluoride (VF), ethylene (E), propylene (P), and a perfluoro(alkyl vinyl ether) (PAVE). Specific examples of PAVE include perfluoro (methyl vinyl ether) (PMVE), perfluoro(ethyl vinyl ether) and perfluoro(propyl vinyl ether).

In certain embodiments, fluoroelastomers can also be produced in an emulsion polymerization process using a water-soluble polymerization initiator and a excess amount of surfactant. The resulting fluoroelastomer may exit the reactor in the form of a latex which must be degassed (e.g., freed from unreacted monomers), coagulated, filtered and washed. Fluoroelastomers can also be produced in a suspension polymerization process, where polymerization is carried out by dispersing one or more monomers, or an organic solvent with monomer dissolved therein, in water and using an oil-soluble organic peroxide. No surfactant or buffer is typically used and fluoroelastomer is produced in the form of polymer particles which may be directly filtered, e.g., without the need for coagulation, and then washed, thus producing a cleaner polymer than that resulting from an emulsion process. Also, the fluoroelastomer polymer chains are substantially free of ionic end groups so that the Mooney viscosity is relatively low and the polymer has improved processability compared to polymer produced by an emulsion process.

In certain embodiments, perfluoroelastomers can be used with the silane modified fillers described herein. Perfluoroelastomers are generally amorphous polymeric compositions having copolymerized units of at least two principal perfluorinated monomers. Generally, one of the principal monomers is a perfluoroolefin while the other is a perfluorovinyl ether. Representative perfluorinated olefins include tetrafluoroethylene and hexafluoropropylene. Suitable perfluorinated vinyl ethers include those of the formula $CF_2=CFO(R_mO)_n(R_kO)_jR_f$ where $R_m$ and $R_k$ are different linear or branched perfluoroalkylene groups of 2-6 carbon atoms, m, n and j are independently 0-10, and $R_f$ is a perfluoroalkyl group having 1-6 carbon atoms. Perfluoroelastomers have achieved outstanding commercial success and are used in a wide variety of applications in which severe environments are encountered, in particular those end uses where exposure to high temperatures and aggressive chemicals occurs. For example, these polymers are often used in seals for aircraft engines, in oil-well drilling devices, and in sealing elements for industrial equipment used at high temperatures. The outstanding properties of perfluoroelastomers can be attributed to the stability and inertness of the copolymerized perfluorinated monomer units that make up the major portion of the polymer backbones in these compositions. Such monomers include tetrafluoroethylene and perfluorinated vinyl ethers. In order to develop elastomeric properties fully, perfluoroelastomers are typically cross-linked, e.g., vulcanized. To this end, a small amount of cure site monomer can be copolymerized with the perfluorinated monomer units.

In other embodiments, poly(perfluoro-alkylene oxides) terminated with polymerizable functional groups can be polymerized to prepare certain polymers, e.g., polyurethanes, having low glass transition temperatures and low-temperature flexibility. For example, poly(perfluoroalkylene oxide) peroxides can be used with ethylenically unsaturated monomers in making block copolymers having good low-temperature flexibility. Fluorinated ethers with nonfunctional terminal moieties are sold under the trademarks "Krytox" and "Fomblin" for use as vacuum pump fluids, see e.g., G. Caporiccio et al., 21 IND. ENG. CHEM. PROD. RES. DEV. 515-19 (1982).

In certain examples, compositions of fluoroelastomers cross-linked with dihydroxypolyfluoroethers may be used. The dihydroxypolyfluoroethers may contain either branched moieties, are random copolymers containing —$CF_2O$— repeating units, or contain partially fluorinated repeat units. In other examples, perfluoropolyether polymers may be prepared as described, for example, in U.S. Pat. No. 5,026,786. These perfluoropolyethers comprise randomly distributed perfluoroxyalkylene units. European Pat. Pub. No. 222,201 describes vulcanizable rubber blends comprising certain perfluoropolyether which can also be used with the coupling agents described herein. These perfluoropolyethers have brominated or fluorinated end groups. European Pat. Pub. No. 310,966 describes rubber blends comprising certain perfluoropolyethers. These perfluoropolyethers comprise perfluoroalkyl end groups.

In certain embodiments, certain classes of fluorinated ether compositions comprising functional fluoroaliphatic mono- and polyethers may be used, as described, for example, in U.S. Pat. No. 5,384,374 and U.S. Pat. No. 5,266,650.

The polymers suitable for use with the silane modified fillers including, but not limited to, fluoroelastomers, perfluoroelastomers and the like, are commercially available from numerous sources including, but not limited to, DuPont Performance Elastomers LLC (Wilmington, Del.), DuPont-Mitsui Fluorochemicals Co. (Japan), AGC Chemicals America (Exton, Pa.), Solvay Solexis (Italy), Daikin Industries (Japan), Zeon Corporation (Japan), Exfluor Research Corporation (Austin, Tex.) and other chemical suppliers.

Figure 13:
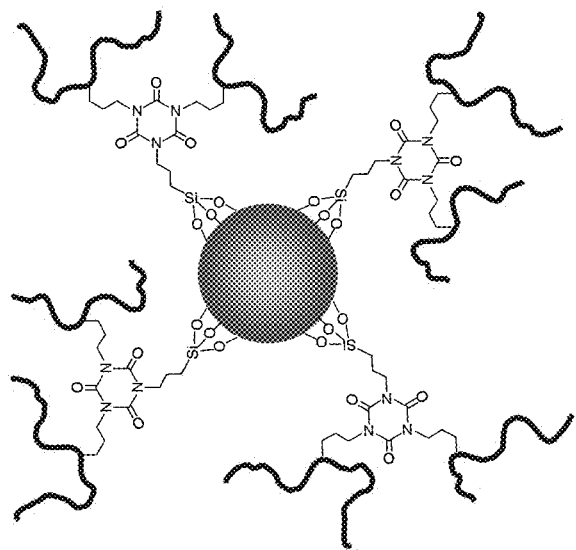
FIG. 13 is an illustration of a filler particle covalently coupled to a polymer through a silane coupling agent, in accordance with certain examples.

In preparing the compositions, the silane coupling agent may be linked to the filler surface in a first step and the resulting product can be reacted with the polymer in a second step. In other examples, the silane coupling agent may be reacted with the polymer in a first step and then reacted with the filler surface in a second step. In yet other examples, the polymer, filler and silane coupling agent may all be mixed or blended together to provide a composition that includes a polymer coupled to a filler through the silane coupling agent. Notwithstanding the exact sequence of event used, the resulting composition includes a filler covalently coupled to a polymer through the silane coupling agent. An illustration of the resulting composition is shown in FIG. 13. In certain examples, free radicals are first generated using suitable species such as, for example, branched alkyl molecules including one or more heteroatoms such as, oxygen, nitrogen or sulfur. In this initiation step, the free radicals may be generated by exposing the alkyl molecules to light, heat, initiators such as peroxides, chlorine gas, bromine or other commonly employed free radical initiators. The formed free radicals may react with the silane-modified fillers to form silane-modified fillers that include a free radical. The free radical filler can react with the polymer in one or a series of propagation steps to covalently couple the polymer to the silane modified filler and/or to generate more free radicals. In one or more termination steps, the free radical filler may react with multiple polymer molecules and result in polymer being covalently coupled to the filler through the silane coupling agent. Such free radical reactions and conditions suitable for performing them will be readily selected by the person of ordinary skill in the art, given the benefit of this disclosure.

Additional components may be used in or with the polymer-silane coupling agent-filler composition. For examples, additives, viscosity modifiers, processing aids and the like may be used. Examples of such additional components include, but are not limited to, antiozonants, antioxidants, plasticizers, resins, flame retardants, lubricants, one or more curing agents such as, for example, sulfur, sulfur donors, activators, accelerators, peroxides, thickeners, thinners, solvents, salts and other materials.

In processing the materials, various devices such as mills, mixers, molds, calendering devices, extruders and the like may be used. For example, the materials may be blended, open milled, mixed with an internal mixer (which may include temperature control to avoid scorching) or otherwise combined in a suitable device. One pass or multi-pass mixing may be used. High shear mixing may be used to obtain good dispersion. The materials may be reworked in one or more additional stages to further assist in mixing. Illustrative molding processes that may be used with the materials include, but are not limited to compression, transfer and injection molding, extrusion and calendering. In compression molding, a preform may be used to provide a desired shape or mass to the resulting material. In injection molding, the material may be injected at high pressure into a mold. Calendering may be used to produce sheets of material. The compounds for calendaring may be used with viscosity modifiers to provide medium or low viscosity materials to facilitate the calendaring process. The materials may also be shaped by extrusion. For example, the material may be forced through a shaping die below a curing temperature to impart a desired shape.

Release agents may be used in the preforms, molds and other parts to facilitate removal of the compressed or produced material from these devices.

The presence of a silane on the surface of the filler can have a great effect on the filler dispersion and resulting mechanical properties of the composition. FIGS. 14A, B and C are schematic views of a polymer filled with the thermally stable silane coupling agent modified silica at different filler concentrations. FIG. 14A shows the local structure of one cluster formed by primary silica aggregates. FIG. 14B shows aggregated filler clusters below the gel point Φ*, and FIG. 14C shows aggregated filler clusters above the gel point Φ*. By modifying the surface of the filler with a silane, and subsequent coupling to a polymer through the silane, a reduction in the Payne effect (also known as the Fletcher-Gent effect) may be achieved. The Payne effect is the non-linearity appearing at small strains (a few tens to a few % strain) due to breakage of the filler three-dimensional network (see FIG. 15 showing the Payne effect for untreated silica filler and silane treated silica filler, where the storage modulus G' is plotted as a function of dynamic strain. When the strain is removed or reduced back to the original level, the network reforms and this process generates a hysteresis. The hysteresis generates heat that can be detrimental for the component lifetime. Adding a silane coupling agent to the filler surface and covalently coupling the modified filler to the polymer can reduce this hysteresis and therefore energy dissipation, which in turn can increase the overall use life of the part or component that is produced from the material.

In certain examples, the compositions disclosed herein may be used in downhole tools and devices such as packers used in extraction of fuels through a wellbore. For example, downhole tools, such as modular wireline tools or drilling tools with evaluation capabilities, that employ probes for engaging the formation and establishing fluid communication may be used to make the pressure measurements and acquire the fluid samples. Fluid is typically drawn into the downhole tool through an inlet in the probe. In some instances, such as for tight, low permeability, formations, sampling probes are often replaced by dual inflatable packer assemblies. Examples of such probe and packer systems are depicted, for example, in U.S. Pat. Nos. 7,392,851, 7,363,970, 7,331,581, 6,186,227, 4,936,139, 4,860,581 and 4,660,637 and assigned to Schlumberger, the entire contents of which are hereby incorporated herein by reference for all purposes. In one configuration, a packer comprises, for example, a resilient element, a housing and a rupture disk. The resilient element is adapted to seal off an annulus of the well when compressed, and the housing is adapted to compress the resilient element in response to a pressure exerted by fluid of the annulus on a piston head of the housing. The housing includes a port for establishing fluid communication with the annulus. The rupture disk is adapted to prevent the fluid in the annulus from entering the port and contacting the piston head until the pressure exerted by the fluid exceeds a predefined threshold and ruptures the rupture disk. In another configuration, dual packer elements may be used with either or both of the packer elements comprising one or more of the materials described herein. For example, packer elements may be spaced apart along a downhole tool conveyed by a wireline in a borehole penetrating a subsurface formation. Although a wireline tool is illustrated, other downhole tools conveyed by drill string, coiled tubing, etc. are also suited for such tasks. When inflated, the packer elements cooperate to seal or isolate a section of the borehole wall, thereby providing a flow area with which to induce fluid flow from the surrounding formation(s). Other packers and elements of packer assemblies may be produced using one or more of the compositions described herein. In one embodiment, the compositions may be used in a swellable packer for open-hole zonal isolation. For example, a fluoroelastomer composition as described herein can be used as the barrier coating for swellable materials to slow down the rate of swelling.

In certain embodiments, the compositions disclosed herein may be used to coat one or more devices such as, for example, a coating on the stator or rotor of a mud motor. For example, the composition may be used in a motor that imparts rotational drive to a drilling assembly. Illustrative mud motors and assemblies using them are described, for example in commonly assigned U.S. Pat. Nos. 7,289,285, 6,419,014, 5,727,641, 5,617,926, 5,311,952, the entire disclosure of each of which is hereby incorporated herein by reference for all purposes. In certain examples, the compositions described herein may be used in a formation tester such as MDT (Modular Formation Dynamics Tester) from Schlumberger, permeability probes, power drive pads and other components and tools commonly used downhole for oilfield and gas exploration.

Certain specific examples are described in more detail below to illustrate further some aspects, features and examples of the materials and compositions described herein.

Example 1

TAIC-silane can be produced by reacting triallylisocyanurate with trimethoxysilane $(MeO)_3SiH$ in the presence of Karstedt catalyst to provide a silane coupling agent having formula (XIX) shown below.

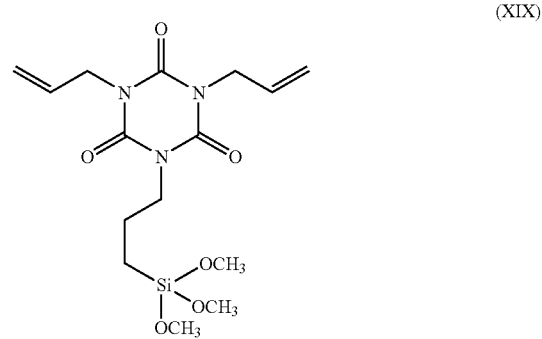 [SMILES: C=CCn1c(=O)n(CC=C)c(=O)n(CCC[Si](OC)(OC)OC)c1=O]

Figure 16A:
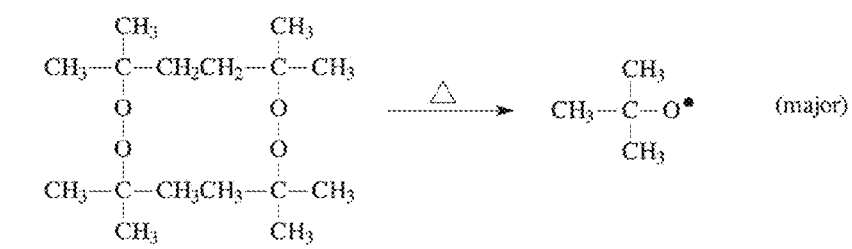
FIGS. 16A-16C are diagrams showing a free radical mechanism by which TAIC-silane modified filler may react with a polymer to covalently couple the polymer to the TAIC-silane modified filler through the silane.
Figure 16A:
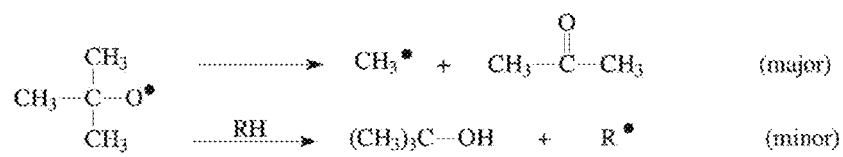
Figure 16A:
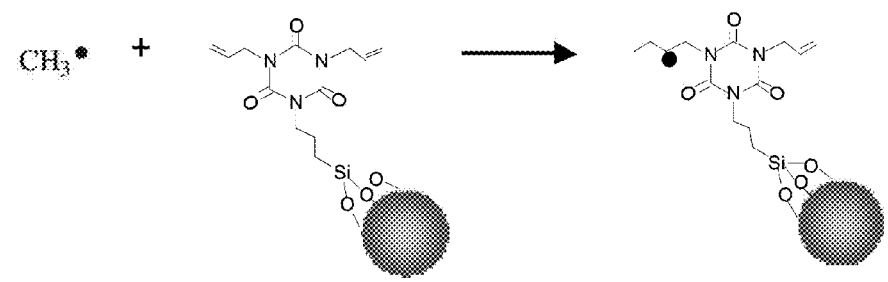
Figure 16B:
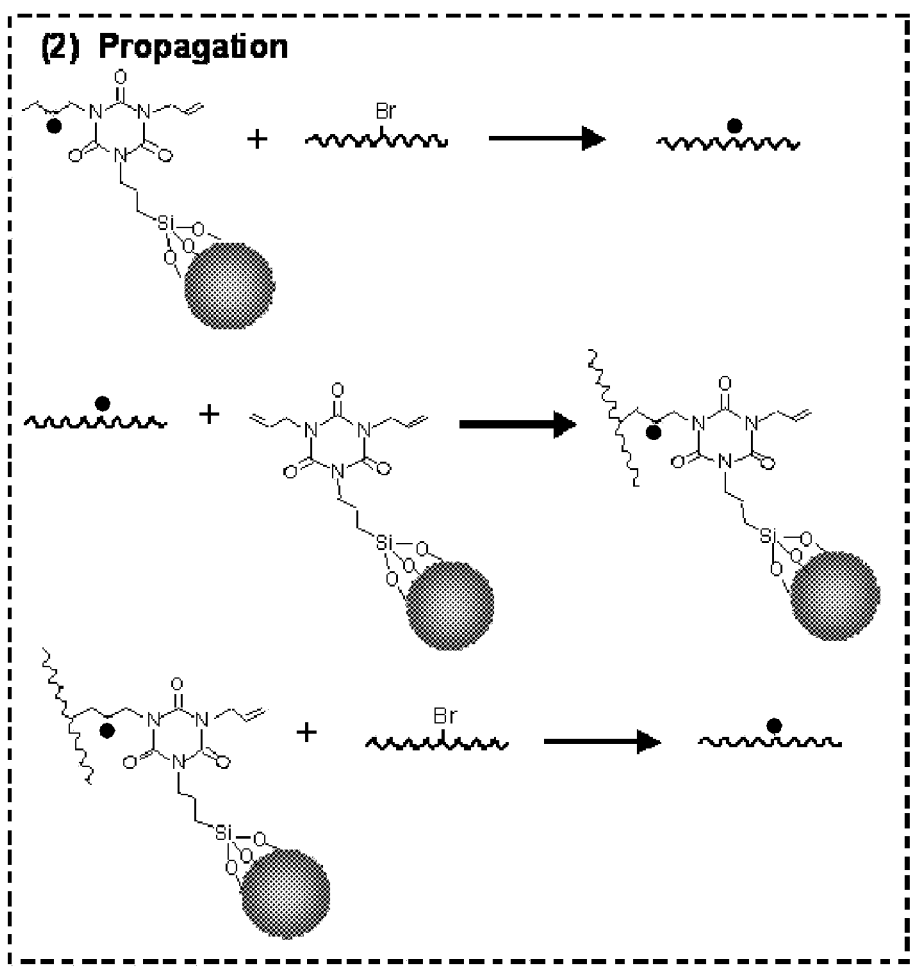
Figure 16C:
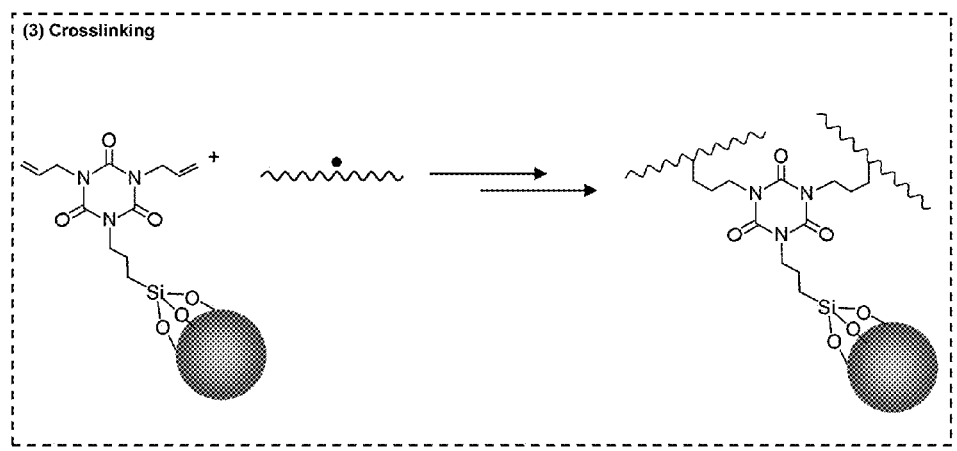

The TAIC-silane of formula (XIX) can be covalently coupled to a filler to provide a TAIC-silane modified filler. The TAIC modified filler can be covalently coupled to a polymer, e.g., a fluoropolymer, by reaction with the polymer through a free radical mechanism (see FIGS. 16A-C). Referring to FIG. 16A, in a first step free radicals can be generated using one or more molecules that are susceptible to free radical formation. Such free radicals may be formed in the presence of an initiator, such as heat, light, peroxides, chlorine gas, bromine or other materials. Once radicals are formed, the silane modified filler may be added to the reaction mixture, and the free radicals can react with the unsaturated site or sites of the silane coupling agent to form radical silane modified fillers. In the propagation steps (see FIG. 16B), polymer molecules may be coupled to the radical silane modified fillers. In the final step, chain termination (FIG. 16C) may occur to provide

Example 2

Figure 17:
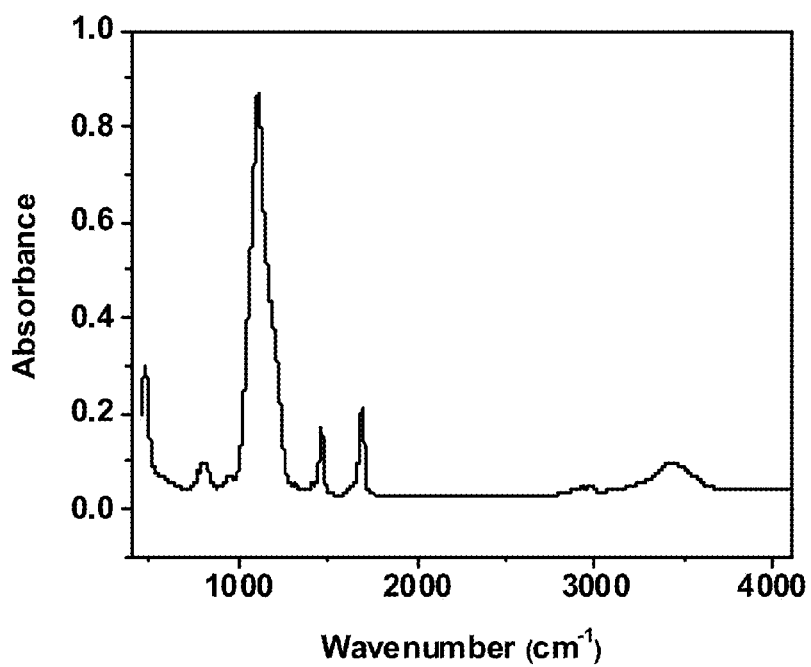
FIG. 17 is an infrared spectrum, in accordance with certain examples.

In one embodiment similar to Example 1, TAIC-silane treated Cab-o-Sil M-5 silica was produced according to the following protocol: To a 250 mL flask, add 2.8 g Cab-o-Sil M-5 silica and 100 mL acetone. Put the flask on a stirring hotplate, and stir until the mixture forms a homogenous suspension. Add 1.9 g TAIC-silane ((VII)(a), where Rn=ethoxy group) while stirring. Heat and keep the suspension to ~45° C., and stir for at least 2 hours. Cool the suspension to room temperature. Two methods of mixing the TAIC-treated silica with a suitable polymer are desirable. For a wet mixing procedure, add the TAIC-silane treated silica filler suspension into an acetone solution of the suitable polymer and stir well until a homogenous mixture is formed. Dry the mixture before compounding with other additives using an internal mixer. For a dry mixing procedure, the TAIC-silane treated silica filler is separated from the solvent via centrifugation and dried before mixing with the polymer and all additives. In the laboratory conditions, the wet mixing procedure yields more favorable mixing results. An infrared spectrum was obtained (see FIG. 17), which confirmed that the TAIC-silane coupling agent reacted with the silica.

Example 3

A TMAIC-silane coupling agent can be produced by reacting trimethallylisocyanurate with trimethoxysilane (MeO)$_3$SiH) in the presence of Karstedt catalyst to provide a silane coupling agent having formula (XX) shown below.

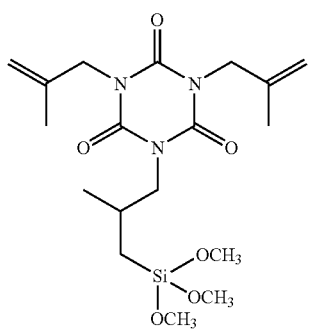

(XX)

The TMAIC-silane of formula (XX) can be covalently coupled to a filler to provide a TMAIC-silane modified filler. The TMAIC modified filler can be covalently coupled to a polymer, e.g., a fluoropolymer, by reaction with the polymer through a free radical mechanism.

Example 4

TAC-silane coupling agent can be produced by reacting triallylcyanurate with trimethoxysilane (MeO)$_3$SiH) in the presence of Karstedt catalyst to provide a silane coupling agent having formula (XXI) shown below.

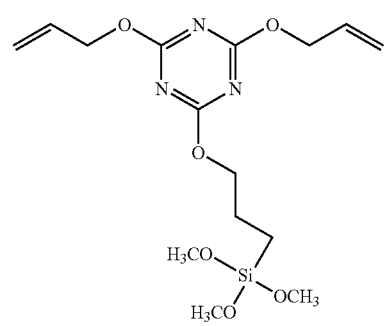

(XXI)

The TAC-silane of formula (XXI) can be covalently coupled to a filler to provide a TAC-silane modified filler. The TAC modified filler can be covalently coupled to a polymer, e.g., a fluoropolymer, by reaction with the polymer through a free radical mechanism.

Example 5

A specific polymer, filler and coupling agent may be mixed together to covalently couple the filler to the polymer. In one example, the specific polymer may be one or more of a fluoropolymer that can be selected from the group consisting of vinylidene fluoride (VDF), tetrafluoroethylene (TFE), hexafluoropropylene (HFP), chlorotrifluoroethylene (CTFE), perfluoro(alkylvinyl ether) (PAVE) including perfluoro(methylvinyl ether) (PMVE), vinyl fluoride (VF), ethylene (E), propylene (P) and the like. Other suitable polymers that may be used alone or in combination with the fluoropolymer include, but are not limited to, polyethylene (PE), polypropylene (PP), styrene butadiene rubber (SBR), ethylene propylene diene monomer (EPDM), nitrile butadiene rubber (NBR), hydrogenated nitrile butadiene rubber (HNBR), silicone, fluorosilicone, and combinations thereof. Tecnoflon P757 (Solvay Solexis), for example, may be used, which is a copolymer of VDF, TFE and HFP.

As the specific filler, one or more of precipitated silica, amorphous silica, vitreous silica, fumed silica, fused silica, quartz, glass, aluminum, aluminum-silicate (e.g., clays), copper, tin, talc, inorganic oxides (e.g. Al$_2$O$_3$, Fe$_2$O$_3$, TiO$_2$, Cr$_2$O$_3$), steel, iron, asbestos, nickel, zinc, silver, lead, marble, chalk, gypsum, barites, graphite, carbon black, treated carbon black such as, for example, silicon treated carbon black and other particles, powders and materials that include, or can be chemically modified to include, one or more surface reactive groups may be used. Fumed silica Cab-o-Sil M5 (Cabot) is one example of a filler than can be used.

Any one or more of the silane coupling agents described herein may be used. For example, TAIC-silane ((VII) (a), where Rn=ethoxy group) can be used as one example.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. A composition comprising a fluoropolymer covalently coupled to a filler through a thermally stable silane coupling agent, the silane coupling agent selected from the group consisting of TAIC-silane, TMAIC-silane, TAC-silane and combinations thereof, in which substantially all of the reactive sites of the filler are covalently coupled to the silane coupling agent.

2. The composition of claim 1, in which the fluoropolymer is selected from the group consisting of vinylidene fluoride (VDF), tetrafluoroethylene (TFE), hexafluoropropylene (HFP), chlorotrifluoroethylene (CTFE), and a perfluoro (alkylvinyl ether) (PAVE).

3. The composition of claim 2, in which the filler is selected from the group consisting of precipitated silica, amorphous silica, vitreous silica, fumed silica, fused silica, quartz, glass, aluminum, aluminum-silicate (e.g., clays), copper, tin, talc, inorganic oxides (e.g. $Al_2O_3$, $Fe_2O_3$, $TiO_2$, $Cr_2O_3$), steel, iron, asbestos, nickel, zinc, silver, lead, marble, chalk, gypsum, barites, graphite, carbon black, treated carbon black.

4. The composition of claim 1, further comprising at least one silane coupling agent having a formula as shown in formulae (XVII)(a)-(XIX)(p).

5. The composition of claim 1, further comprising at least one of an additive a viscosity modifier or a processing aid.

* * * * *